(12) United States Patent
Laflamme et al.

(10) Patent No.: US 8,815,593 B2
(45) Date of Patent: Aug. 26, 2014

(54) INDUCTION OF HUMAN EMBRYONIC STEM CELL DERIVED CARDIAC PACEMAKER OR CHAMBER-TYPE CARDIOMYOCYTES BY MANIPULATION OF NEUREGULIN SIGNALING

(71) Applicant: University of Washington, Seattle, WA (US)

(72) Inventors: Michael A. Laflamme, Seattle, WA (US); Wei-Zhong Zhu, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/061,200

(22) Filed: Oct. 23, 2013

(65) Prior Publication Data
US 2014/0087460 A1  Mar. 27, 2014

Related U.S. Application Data

(62) Division of application No. 12/611,569, filed on Nov. 3, 2009, now Pat. No. 8,603,817.

(60) Provisional application No. 61/110,793, filed on Nov. 3, 2008.

(51) Int. Cl.
*C12N 5/00* (2006.01)
*C12N 5/071* (2010.01)
*A61K 35/12* (2006.01)

(52) U.S. Cl.
CPC ........ *C12N 5/0657* (2013.01); *C12N 2501/155* (2013.01); *C12N 2510/00* (2013.01); *C12N 2502/13* (2013.01); *C12N 2501/11* (2013.01); *A61K 35/12* (2013.01); *C12N 2506/02* (2013.01); *C12N 2501/16* (2013.01); *C12N 2501/13* (2013.01); *C12N 2533/90* (2013.01); *C12N 2501/115* (2013.01)
USPC .......................................... 435/377; 435/325

(58) Field of Classification Search
USPC ................................................ 435/377, 325
See application file for complete search history.

(56) References Cited

U.S. PATENT DOCUMENTS

| 7,611,852 | B2 | 11/2009 | Thomson et al. | |
|---|---|---|---|---|
| 2003/0211088 | A1* | 11/2003 | Field | 424/93.21 |
| 2004/0106095 | A1 | 6/2004 | Thomson et al. | |
| 2007/0239136 | A1 | 10/2007 | White et al. | |
| 2008/0089874 | A1 | 4/2008 | Li et al. | |

FOREIGN PATENT DOCUMENTS

WO  2006/021459  3/2006

OTHER PUBLICATIONS

Gassanov et al., "Endothelin Induces Differentiation of ANP-EGFP Expressing Embryonic Stem Cells Towards a Pacemaker Phenotype," The FASEB Journal pp. 1-19 (2004).
Kim et al., "Activation of MEK-ERK by Heregulin-B1 Promotes the Development of Cardiomyocytes Derived from ES Cells," Biochemical and Biophysical Research Communications 361(3):732-8 (2007).
Kolossov et al., "Identification and Characterization of Embryonic Stem Cell-Derived Pacemaker and Atrial Cardiomyocytes," The FASEB Journal pp. 1-25 (2005).
Maltsev et al., "Embryonic Stem Cells Differentiate In Vitro Into Cardiomyocytes Representing Sinusnodal, Atrial and Ventricular Cell Types," Mech Dev. 44(1):41-50 (1993).
Müller et al., "Selection of Ventricular-Like Cardiomyocytes from ES Cells In Vitro," The FASEB Journal 14:2540-8 (2000).
Ruhparwar et al., "Enrichment of Cardiac Pacemaker-Like Cell: Neuregulin-1 and Cyclic AMP Increase If-Current Density and Connexin 40 mRNA Levels in Fetal Cardiomyocytes," Med Bio Eng Comput 45:221-7 (2007).
Wang et al., "Neuregulin-1 Promotes Cardiomyocyte Differentiation of Genetically Engineered Embryonic Stem Cell Clones," BMB Reports pp. 699-704 (2008).
White et al., "Embryonic Stem Cells Form an Organized, Functional Cardiac Conduction System In Vitro," AJP-Heart Circ Physiol 288:H670-H679 (2005).
Wobus et al., "Retinoic Acid Accelerates Embryonic Stem Cell-Derived Cardiac Differentiation and Enhances Development of Ventricular Cardiomyocytes," J Mol Cell Cardiol. 29(6):1525-39 (1997).
Laflamme et al., Nature Biotechnology, 25(9):1015-1024 (2007). "Cardiomyocytes derived from human embryonic stem cells in pro-survival factors enhance function of infarcted rat hearts."
Chung et al., Molecular Pharmacology, 71(6):1494-1502 (2007). "Interaction and inhibitory cross-talk between endothelin and ErbB receptors in the adult heart."
Liang et al., Journal of Biological Chemistry, 276(32):30245-30253 (2001). "The transcription factors GATA4 and GATA6 regulate cardiomyocyte hypertrophy in vitro and in vivo."

\* cited by examiner

*Primary Examiner* — Karen Cochrane Carlson
*Assistant Examiner* — Natalie Moss
(74) *Attorney, Agent, or Firm* — Nixon Peabody LLP

(57) ABSTRACT

The present invention is directed to methods of producing cardiomyocytes having a nodal/pacemaker phenotype and cardiomyocytes having an atrial/ventricular phenotype. Isolated populations of nodal/pacemaker and atrial/ventricular cardiomyocytes are also disclosed. Methods of treating a subject having cardiac arrhythmia and a subject in need of cardiac tissue repair using the isolated populations of nodal/pacemaker cardiomyocytes and atrial/ventricular cardiomyocytes, receptively, are also disclosed.

18 Claims, 6 Drawing Sheets

INDUCTION OF HUMAN EMBRYONIC STEM CELL DERIVED CARDIAC PACEMAKER OR CHAMBER-TYPE CARDIOMYOCYTES BY MANIPULATION OF NEUREGULIN SIGNALING

CROSS-REFERENCE TO RELATED APPLICATIONS

This application is a divisional application of U.S. patent application Ser. No. 12/611,569 filed on Nov. 3, 2009, which claims benefit under 35 U.S.C. §119(e) of U.S. Provisional Patent Application No. 61/110,793 filed on Nov. 3, 2008, the contents of each of which are incorporated herein by reference in their entireties.

GOVERNMENT SUPPORT

This invention was made with government support under grant numbers K08 HL080431 and R01 HL064387 awarded by the National Institutes of Health and National Heart, Lung, and Blood Institute. The government has certain rights in this invention.

FIELD OF THE INVENTION

The present invention relates to methods of producing nodal/pacemaker and atrial/ventricular cardiomyocytes. The invention further relates to methods of treating cardiac arrhythmias and improving cardiac tissue repair and function using the nodal/pacemaker and atrial/ventricular cell populations, respectively.

BACKGROUND OF THE INVENTION

Prospects for Cell-Based Cardiac Therapies with Cardiomyocytes from Pluripotent Human Cells The muscle lost after a myocardial infarction is replaced with non-contractile scar tissue, often initiating heart failure. Whole-organ cardiac transplantation is the only currently available clinical means of replacing the lost muscle, but this option is limited by the inadequate supply of donor hearts. Given this, much attention has recently been directed at cell transplantation strategies as an alternate means of ameliorating cardiac injury (Laflamme & Murry, "Regenerating the Heart," *Nat Biotechnol* 23(7):845-856 (2005); Dimmeler et al., "Unchain My Heart: The Scientific Foundations of Cardiac Repair," *J Clin Invest* 115(3):572-583 (2005); Laflamme et al., "Cell-Based Cardiac Repair: Pathophysiologic Mechanisms," *Annual Rev Pathol* 2:307-39 (2007); Rubart et al., "Cardiac Regeneration: Repopulating the Heart," *Annu Rev Physiol* 68:29-49 (2006)). A number of candidate cell types have been considered, including skeletal myoblasts (Menasche et al., "Autologous Skeletal Myoblast Transplantation for Severe Postinfarction Left Ventricular Dysfunction," *J Am Coll Cardiol* 41(7):1078-1083 (2003); Murry et al., "Skeletal Myoblast Transplantation for Repair of Myocardial Necrosis," *J Clin Invest* 98(11):2512-2523 (1996); Taylor et al., "Regenerating Functional Myocardium: Improved Performance After Skeletal Myoblast Transplantation," *Nat Med* 4(8):929-933 (1998)), bone marrow-derived hematopoietic stem cells (Orlic et al., "Bone Marrow Cells Regenerate Infarcted Myocardium," *Nature* 410(6829):701-705 (2001)), mesenchymal stem cells (Shake et al., "Mesenchymal Stem Cell Implantation in a Swine Myocardial Infarct Model: Engraftment and Functional Effects," *Ann Thorac Surg* 73(6): 1919-1926 (2002); Toma et al., "Human Mesenchymal Stem Cells Differentiate to a Cardiomyocyte Phenotype in the Adult Murine Heart," *Circulation* 105(1):93-98 (2002); Min et al., "Significant Improvement of Heart Function By Co-transplantation of Human Mesenchymal Stem Cells and Fetal Cardiomyocytes in Postinfarcted Pigs," *Ann Thorac Surg* 74(5):1568-1575 (2002); Mangi et al., "Mesenchymal Stem Cells Modified With Akt Prevent Remodeling and Restore Performance of Infarcted Hearts," *Nat Med* 9(9):1195-1201 (2003)), and intrinsic cardiac stem cells (Beltrami et al., "Adult Cardiac Stem Cells Are Multipotent and Support Myocardial Regeneration," *Cell* 114(6):763-776 (2003); Oh et al., "Cardiac Progenitor Cells From Adult Myocardium: Homing, Differentiation, and Fusion After Infarction," *Proc Natl Acad Sci USA* 100(21):12313-12318 (2003); Laugwitz et al., "Postnatal isl1+ Cardioblasts Enter Fully Differentiated Cardiomyocyte Lineages," *Nature* 433(7026):647-653 (2005); Smith et al., "Regenerative Potential of Cardiosphere-Derived Cells Expanded From Percutaneous Endomyocardial Biopsy Specimens," *Circulation* 115(7):896-908 (2007)), but pluripotent hESCs have a number of particularly attractive properties for such applications. First, in contrast to many adult stem cell types for which this capacity is controversial, hESCs have unquestioned cardiomyogenic potential (Xu et al., "Characterization and Enrichment of Cardiomyocytes Derived From Human Embryonic Stem Cells," *Circ Res* 91(6):501-508 (2002); Mummery et al., "Differentiation of Human Embryonic Stem Cells to Cardiomyocytes: Role of Coculture With Visceral Endoderm-Like Cells," *Circulation* 107(21):2733-2740 (2003); Kehat et al., "Human Embryonic Stem Cells Can Differentiate Into Myocytes With Structural and Functional Properties of Cardiomyocytes," *J Clin Invest* 108(3):407-414 (2001)). Indeed, an efficient protocol that reliably generates large quantities of ~90% cardiomyocytes from hESCs, has greatly facilitated work with these cells (Laflamme et al., "Cardiomyocytes Derived From Human Embryonic Stem Cells in Pro-Survival Factors Enhance Function of Infarcted Rat Hearts," *Nat Biotechnol* 25(9):1015-1024 (2007)). Second, hESCs can be isolated and maintained by well-established protocols, and they are tremendously scaleable. Undifferentiated hESCs retain their phenotype through as many as one hundred population doublings, and, after differentiation, hESC-CMs exhibit robust proliferative capacity both in vitro (Xu et al., "Characterization and Enrichment of Cardiomyocytes Derived From Human Embryonic Stem Cells," *Circ Res* 91(6):501-508 (2002); McDevitt et al., "Proliferation of Cardiomyocytes Derived From Human Embryonic Stem Cells is Mediated Via the IGF/PI 3-kinase/Akt Signaling Pathway," *J Mol Cell Cardiol* 39(6):865-873 (2005); Snir et al., "Assessment of the Ultrastructural and Proliferative Properties of Human Embryonic Stem Cell-Derived Cardiomyocytes," *Am J Physiol Heart Circ Physiol* 285(6):H2355-2363 (2003)) and in vivo (Laflamme et al., "Formation of Human Myocardium in the Rat Heart From Human Embryonic Stem Cells," *Am J Pathol* 167(3):663-671 (2005)). Third, a number of recent reports have demonstrated that hESC-CMs survive after transplantation into infarcted rodent hearts, form stable cardiac implants, and preserve contractile function (Laflamme et al., "Cardiomyocytes Derived From Human Embryonic Stem Cells in Pro-Survival Factors Enhance Function of Infarcted Rat Hearts," *Nat Biotechnol* 25(9):1015-1024 (2007); Caspi et al., "Transplantation of Human Embryonic Stem Cell-Derived Cardiomyocytes Improves Myocardial Performance in Infarcted Rat Hearts," *J Am Coll Cardiol* 50(19):1884-1893 (2007); van Laake et al., "Human Embryonic Stem Cell-Derived Cardiomyocytes Survive and Mature in the Mouse Heart and Transiently Improve Function After Myocardial Infarction," *Stem Cell Research* 1(1):9-24 (2007)). Finally, although the need to use immunosuppression to overcome allorejection of hESC-derivatives has often been raised as a limitation of these cells, the recently reported ESC-like induced pluripotent stem cells (iPSCs) represent a potential solution to this problem (Takahashi et al., "Induction of Pluripotent Stem Cells From Adult Human Fibroblasts By Defined Factors," *Cell* 131(5):861-872 (2007); Park et al., "Reprogramming of Human Somatic Cells to Pluripotency With Defined Factors," *Nature* (2007); Yu et al., "Induced Pluripotent Stem Cell Lines Derived From Human Somatic Cells," *Science* 318(5858):1917-1920 (2007)). iPSCs are generated by reprogramming human adult fibroblasts and so may be used in an autologous fashion. iPSCs can be induced to differentiate into cardiomyocytes using the same techniques as those reported for hESCs (Takahashi et al., "Induction of Pluripotent Stem Cells From Adult Human Fibroblasts By Defined Factors," *Cell* 131(5):861-872 (2007)).

Often overlooked is another potential application for cell-based therapies: the development of a "biological pacemaker". An estimated three million people worldwide currently have an implanted artificial pacemaker, and up to 600,000 receive new ones each year (Wood et al., "Cardiology Patient Pages. Cardiac Pacemakers From the Patient's Perspective," *Circulation* 105(18):2136-2138 (2002)). While these devices successfully treat a broad range of electrophysiological abnormalities, they do have shortcomings including increased susceptibility to infection, a finite battery life, significant patient discomfort, and lack of intrinsic responsiveness to neurohumoral signaling. These limitations have led to recent interest in gene- and/or cell-based therapies as an alternate strategy (Miake et al., "Biological Pacemaker Created By Gene Transfer," *Nature* 419(6903):132-133 (2002); Qu et al., "Expression and Function of a Biological Pacemaker in Canine Heart," *Circulation* 107(8):1106-1109 (2003); Plotnikov et al., "Biological Pacemaker Implanted in Canine Left Bundle Branch Provides Ventricular Escape Rhythms That Have Physiologically Acceptable Rates," *Circulation* 109(4): 506-512 (2004); Potapova et al., "Human Mesenchymal Stem Cells as a Gene Delivery System to Create Cardiac Pacemakers," *Circ Res* 94(7):952-959 (2004)).

Signaling Pathways Involved in Development of the Cardiac Pacemaking and Conduction Systems Elegant work in developmental model systems has implicated a variety of signaling molecules as important in the development of "specialized" cardiac subtypes, including neuregulin (NRG) (Hertig et al., "Synergistic Roles of Neuregulin-1 and Insulin-Like Growth Factor-I in Activation of the Phosphatidylinositol 3-Kinase Pathway and Cardiac Chamber Morphogenesis," *J Biol Chem* 274(52):37362-37369 (1999); Rentschler et al., "Visualization and Functional Characterization of the Developing Murine Cardiac Conduction System," *Development* 128(10): 1785-1792 (2001); Rentschler et al., "Neuregulin-1 Promotes Formation of the Murine Cardiac Conduction System," *Proc Natl Acad Sci USA* 99(16):10464-10469 (2002); Ruhparwar et al., "Prospects for Biological Cardiac Pacemaker Systems," *Pacing Clin Electrophysiol* 26(11):2069-2071 (2003)), endothelin (Gourdie et al., "Endothelin-Induced Conversion of Embryonic Heart Muscle Cells Into Impulse-Conducting Purkinje Fibers," *Proc Natl Acad Sci USA* 95(12):6815-6818 (1998); Hyer et al., "Induction of Purkinje Fiber Differentiation By Coronary Arterialization," *Proc Natl Acad Sci USA* 96(23):13214-13218 (1999); Cheng et al., "Development of the Cardiac Conduction System Involves Recruitment Within a Multipotent Cardiomyogenic Lineage," *Development* 126 (22):5041-5049 (1999)), retinoic acid (Xavier-Neto et al., "A Retinoic Acid-Inducible Transgenic Marker of Sin θ-Atrial Development in the Mouse Heart," *Development* 126(12): 2677-2687 (1999); Rosenthal et al., "From the Bottom of the Heart: Anteroposterior Decisions in Cardiac Muscle Differentiation," *Curr Opin Cell Biol* 12(6):742-746 (2000); Xavier-Neto et al., "Retinoid Signaling and Cardiac Anteroposterior Segmentation," *Genesis* 31(3):97-104 (2001); Hochgreb et al., "A Caudorostral Wave of RALDH2 Conveys Anteroposterior Information to the Cardiac Field," *Development* 130(22):5363-5374 (2003)) and Wnt family ligands (Bond et al., "Wnt11 and Wnt7a Are Up-Regulated in Association With Differentiation of Cardiac Conduction Cells In Vitro and In Vivo," *Dev Dyn* 227(4):536-543 (2003); Tabibiazar et al., "Transcriptional Profiling of the Heart Reveals Chamber-Specific Gene Expression Patterns," *Circ Res* 93(12):1193-1201 (2003); Monaghan et al., "Dickkopf Genes are Co-ordinately Expressed in Mesodermal Lineages," *Mech Dev* 87(1-2):45-56 (1999)). Several recent reviews have presented detailed descriptions of the development of the cardiac pacemaker and conduction systems (Gourdie et al., "Development of the Cardiac Pacemaking and Conduction System," *Birth Defects Res Part C Embryo Today* 69(1):46-57 (2003); Christoffels et al., "Architectural Plan for the Heart: Early Patterning and Delineation of the Chambers and the Nodes," *Trends Cardiovasc Med* 14(8): 301-307 (2004)). Broadly speaking, there are three fundamental events in their formation: First, a population of cardiomyocytes in the posterior, sinoatrial pole of the early embryonic heart tube assumes a nodal/pacemaker-like phenotype and acts as a dominant pacemaker, driving rhythmic propagation along the posterior-to-anterior axis (Kamino K, "Optical Approaches to Ontogeny of Electrical Activity and Related Functional Organization During Early Heart Development," *Physiol Rev* 71(1):53-91 (1991); Satin et al., "Development of Cardiac Beat Rate in Early Chick Embryos is Regulated By Regional Cues," *Dev Biol* 129(1):103-113 (1988)). Retinoid signaling has been implicated as important in establishing this polarity (Xavier-Neto et al., "A Retinoic Acid-Inducible Transgenic Marker of Sin θ-Atrial Development in the Mouse Heart," *Development* 126(12):2677-2687 (1999); Rosenthal et al., "From the Bottom of the Heart: Anteroposterior Decisions in Cardiac Muscle Differentiation," *Curr Opin Cell Biol* 12(6):742-746 (2000); Xavier-Neto et al., "Retinoid Signaling and Cardiac Anteroposterior Segmentation," *Genesis* 31(3):97-104 (2001); Hochgreb et al., "A Caudorostral Wave of RALDH2 Conveys Anteroposterior Information to the Cardiac Field," *Development* 130 (22):5363-5374 (2003)). Second, while conduction velocity generally increases along the looping heart tube, specialized regions (specifically, the AV canal, sinoatrial pole, and outflow tract) retain the comparatively slow propagation of the early tube heart (de Jong et al., "Persisting Zones of Slow Impulse Conduction in Developing Chicken Hearts," *Circ Res* 71(2):240-250 (1992); Arguello et al., "Electrophysiological and Ultrastructural Study of the Atrioventricular Canal During the Development of the Chick Embryo," *J Mol Cell Cardiol* 18(5):499-510 (1986)). Despite its importance, surprisingly little is known about the identity of the inductive cues driving this particular development. It results in sequential activation of the atrial and ventricular segments and may improve the pumping efficiency of the heart tube, because the slowly-conducting segments function as sphincter-like valves. Third, around the time of chamber septation, the fast cardiac conduction system (i.e., the His-Purkinje system) is recruited from "working" ventricular myocytes. Two factors released by endothelial cells have been implicated in this induction, endothelin (Gourdie et al., "Endothelin-Induced Conversion of Embryonic Heart Muscle Cells Into Impulse-Conducting Purkinje Fibers," *Proc Natl Acad Sci USA* 95(12):6815-6818 (1998); Hyer et al., "Induction of Purkinje Fiber Differentiation By Coronary Arterialization," *Proc Natl Acad Sci USA* 96(23):13214-13218 (1999); Cheng et al., "Development of the Cardiac Conduction System Involves Recruitment Within a Multipotent Cardiomyogenic Lineage," *Development* 126(22):5041-5049 (1999)) and neuregulin (NRG) (Rentschler et al., "Visualization and Functional Characterization of the Developing Murine Cardiac Conduction System," *Development* 128(10):1785-1792 (2001)).

While the precise details regarding the timing and identity of inductive cues vary by species, this general sequence of events (early fate decision regarding pacemaker vs. working atrial or ventricular cardiomyocyte→emergence of specialized slower-conducting nodal centers→Purkinje-His conduction system differentiation) appears conserved across vertebrate cardiac morphogenesis.

Neuregulin/ErbB Signaling in Cardiac Development and Subtype Specialization.

The neuregulins (NRG1-4) are members of the epidermal growth factor family that exert diverse biologic effects via the tyrosine receptor kinases ErbB2, ErbB3, and ErbB4. Very little is known about the functions of NRG2-4, but signaling by the NRG1 ligand is known to serve important and diverse functions in both cardiac development and postnatal function (for a comprehensive review of its role in the adult heart, see Negro et al., "Essential Roles of Her2/erbB2 in Cardiac Development and Function," *Recent Prog Horm Res* 59:1-12 (2004); Lemmens et al., "Role of Neuregulin-1/ErbB Signaling in Cardiovascular Physiology and Disease: Implications for Therapy of Heart Failure," *Circulation* 116(8):954-960 (2007); Garratt et al., "ErbB2 Pathways in Heart and Neural Diseases," *Trends Cardiovasc Med* 13(2):80-86 (2003); Iwamoto et al., "ErbB and HB-EGF Signaling in Heart Development and Function," *Cell Struct Funct* 31(1):1-14 (2006)). NRG1/ErbB signaling is remarkably complex: the 1.4 Mb NRG1 gene encodes for at least 15 ligand isoforms, which are classified based on their type of EGF domain ("α" or "β") and N-terminal region (types I, II, or III). Importantly, recombinant peptides consisting of the EGF-like domain (i.e., NRG1-α or -β) alone are sufficient to activate the appropriate ErbB receptors and have been used in most studies to date. All bioactive NRG1 ligands can bind to both ErbB3 and ErbB4 receptors, which results in receptor homo- or heterodimerization and activation of diverse downstream signal transduction cascades (Falls D L, "Neuregulins: Functions, Forms, and Signaling Strategies," *Exp Cell Res* 284(1):14-30 (2003); Holbro et al., "ErbB Receptors: Directing Key Signaling Networks Throughout Life," *Annu Rev Pharmacol Toxicol* 44:195-217 (2004)). Adding further complexity, there is another ErbB family member, the "orphan" receptor ErbB2, that lacks ligand binding capacity, but can mediate downstream signaling upon activation via heterodimerization with ErbB3 or ErbB4. Reciprocally, ErbB3 can bind NRG1 but lacks intrinsic kinase activity, and so this isoform must also heterodimerize to function.

Work in the murine model has demonstrated the importance of NRG1/ErbB signaling in early cardiac development. In the murine embryonic tube heart (likely a state of maturation similar to hESC-CMs), NRG1 is strongly expressed by the ventricular endocardium (and weakly by the atrial endocardium) (Meyer et al., "Multiple Essential Functions of Neuregulin in Development," *Nature* 378(6555):386-390 (1995); Kramer et al., "Neuregulins With an Ig-Like Domain Are Essential For Mouse Myocardial and Neuronal Development," *Proc Natl Acad Sci USA* 93(10):4833-4838 (1996); Corfas et al., "Differential Expression of ARIA Isoforms in the Rat Brain," *Neuron* 14(1):103-115 (1995); Zhao et al., "Selective Disruption of Neuregulin-1 Function in Vertebrate Embryos Using Ribozyme-tRNA Transgenes," *Development* 125(10):1899-1907 (1998)), while adjacent cardiomyocytes express ErbB2 and ErbB4 receptors but not NRG 1 ligand (Meyer et al., "Multiple Essential Functions of Neuregulin in Development," *Nature* 378(6555):386-390 (1995); Gassmann et al., "Aberrant Neural and Cardiac Development in Mice Lacking the ErbB4 Neuregulin Receptor," *Nature* 378 (6555):390-394 (1995); Lee et al., "Requirement for Neuregulin Receptor ErbB2 in Neural and Cardiac Development," *Nature* 378(6555):394-398 (1995)). Of note, NRG1-, ErbB2-, and ErbB4-null mice all die midway through embryogenesis (~embryonic day 10) with an almost identical cardiac malformation, a failure to form ventricular trabeculae (Meyer et al., "Multiple Essential Functions of Neuregulin in Development," *Nature* 378(6555):386-390 (1995); Kramer et al., "Neuregulins With an Ig-Like Domain Are Essential For Mouse Myocardial and Neuronal Development," *Proc Natl Acad Sci USA* 93(10):4833-4838 (1996); Corfas et al., "Differential Expression of ARIA Isoforms in the Rat Brain," *Neuron* 14(1):103-115 (1995); Zhao et al., "Selective Disruption of Neuregulin-1 Function in Vertebrate Embryos Using Ribozyme-tRNA Transgenes," *Development* 125(10):1899-1907 (1998); Gassmann et al., "Aberrant Neural and Cardiac Development in Mice Lacking the ErbB4 Neuregulin Receptor," *Nature* 378(6555):390-394 (1995)). These results indicate a requirement for NRG1/ErbB signaling, likely via ErbB2/ErbB4 heterodimers, in this very early event in ventricular maturation. Interestingly, this defect in cardiac development is phenocopied in mice deficient in the fast sodium channel (SCN5A) (Papadatos et al., "Slowed Conduction and Ventricular Tachycardia After Targeted Disruption of the Cardiac Sodium Channel Gene Scn5a," *Proc Natl Acad Sci USA* 99(9):6210-6215 (2002)), a finding which has led to speculation that electrophysiological abnormalities in the NRG1/ErbB mutants may be responsible for the latter's phenotype (Garratt A N, ""To Erb-B or Not to Erb-B . . . " Neuregulin-1/ErbB Signaling in Heart Development and Function," *J Mol Cell Cardiol* 41(2):215-218 (2006)).

NRG1/ErbB signaling has been implicated in the differentiation of the specialized cardiac conduction system. Prior work in the avian model had implicated another endothelial-released cytokine, endothelin, as inducing Purkinje fiber specialization by "working" ventricular cardiomyocytes. To determine whether endothelin or other factors might mediate similar effects in the developing mouse heart, Rentschler et al., "Visualization and Functional Characterization of the Developing Murine Cardiac Conduction System," *Development* 128(10):1785-1792 (2001), employed the 'CCS-lacZ' (i.e., engrailed lacZ) transgenic mouse in which β-galactosidase is expressed in the cardiac conduction system. Using this convenient readout in an organ culture model, these authors found that, while application of endothelin had no effect, NRG1 greatly expanded β-galactosidase-expressing cardiac conduction system structures in an mouse organ culture model (Rentschler et al., "Neuregulin-1 Promotes Formation of the Murine Cardiac Conduction System," *Proc Natl Acad Sci USA* 99(16):10464-10469 (2002)). Subsequently, a number of groups have looked for similar effects in primary or murine ESC-derived embryonic cardiomyocytes with conflicting results, variably reporting that pacemaker or conduction system differentiation can be induced by NRG1 (Ruhparwar et al., "Enrichment of Cardiac Pacemaker-Like Cells Neuregulin-1 and Cyclic AMP Increase I(f)-Current Density and Connexin 40 mRNA Levels in Fetal Cardiomyocytes," *Med Biol Eng Comput* 45(2):221-227 (2007)), both endothelin and NRG1 (Patel et al., "Endothelin-1 and Neuregulin-1 Convert Embryonic Cardiomyocytes Into Cells of the Conduction System in the Mouse," *Dev Dyn* 233(1):20-28 (2005)), or endothelin but not NRG1 (Gassanov et al., "Endothelin Induces Differentiation of ANP-EGFP Expressing Embryonic Stem Cells Towards a Pacemaker Phenotype," *Faseb J* 18(14):1710-1712 (2004)). One caveat related to the latter studies is that they have sometimes tended to blur endpoints for cardiac pacemaker (e.g., sinoatrial) and conduction (e.g., Purkinje) system differentiation, which, as discussed in the preceding section, are known to be spatially and temporally distinct events in cardiac development. This may account in part for their ostensibly different conclusions.

The present invention is directed to overcoming these and other deficiencies in the art.

SUMMARY OF THE INVENTION

A first aspect of the present invention is directed to a method of producing cardiomyocytes having a nodal/pacemaker phenotype. This method involves culturing stem cells under conditions effective to produce cardiomyocytes and contacting the cardiomyocytes with an antagonist of neuregulin-1 or an antagonist of ErbB under conditions effective to induce the production of cardiomyocytes having a nodal/pacemaker phenotype A second aspect of the present invention is directed to an isolated population of nodal/pacemaker cardiomyocytes. This isolated population of cardiomyocytes is characterized by a spontaneous firing rate of >90 bpm and a slow, biphasic action potential upstroke of <15V/s.

A third aspect of the present invention is directed to a method of treating cardiac arrhythmia in a subject. This method involves providing an isolated population of nodal/pacemaker cardiomyocytes of the present invention and delivering the isolated population of nodal/pacemaker cardiomyocytes to the subject under conditions effective to treat the cardiac arrhythmia.

A fourth aspect of the present invention is directed to a method of producing cardiomyocytes having an atrial/ventricular phenotype. This method involves culturing stem cells under conditions effective to produce cardiomyocytes and contacting the cardiomyocytes with a neuregulin-1 agonist, neuregulin-1 mimetic, or a related agonist of an ErbB receptor under conditions effective to induce the production of cardiomyocytes having an atrial/ventricular phenotype.

A fifth aspect of the present invention is directed to an isolated population of atrial/ventricular cardiomyocytes.

A sixth aspect of the present invention is directed to a method of improving cardiac tissue repair or cardiac organ function in a subject. This method involves providing an isolated population of atrial/ventricular cardiomyocytes of the present invention and delivering the isolated atrial/ventricular cardiomyocytes to the subject under conditions effective to improve cardiac tissue repair or cardiac organ function.

Cell-based therapies have tremendous promise in ameliorating or even reversing serious cardiac diseases. Still, it will almost certainly prove insufficient to merely differentiate stem cells into admixed cardiomyocytes. To ensure proper host-graft integration and attenuate the risk of arrhythmogenesis following cell transplantation, the field will need to guide the differentiation of stem cells in the correct cardiac subtypes for any given clinical application. The present invention is responsive to this need by providing a means to derive enriched populations of nodal/pacemaker cells (e.g., for application as a biological pacemaker) or working, chamber-specific cardiomyocytes (e.g., for replacement of lost ventricular muscle following an infarct).

BRIEF DESCRIPTION OF THE DRAWINGS

FIG. 2C is a photomicrograph showing a patch-clamp electrode (arrow, upper panel) on a representative EGFP+ cell, and its corresponding nodal-type AP recording (lower panel). 20 of 21 EGFP+ hESC-CMs showed a nodal-like AP phenotype, versus only 2 of 20 EGFP− myocytes. FIG. 2D shows histogram plots indicating the number of EGFP+ (top plot) and EGFP− (bottom plot) hESC-CMs exhibiting any given maximal upstroke velocity (dV/dtmax). While virtually all of the EGFP+ putative nodal cells had a dV/dtmax<15 V/s, the EGFP− cells (which likely include both working-type and non-transduced cells) exhibited a wide range of dV/dtmax values.

FIGS. 3B and 3C are immunofluorescence images of representative hESC-CMs, all of which expressed β-myosin heavy chain (β-MHC) (FIGS. 3B and 3C, left panels) as well as ErbB2 (FIG. 3B, middle panel) and ErbB4 (FIG. 3C, middle panel). Relatively few non-cardiac cells (arrow) showed ErbB expression. Bar=25 µm. Immunoblots for phosphorylated and total Akt and ERK (p42 and p44 isoforms) kinases in hESC-CM cultures are shown in FIG. 3D. Treatment with NRG-1β agonist ("NRG ligand") resulted in the activation of both kinases, an effect that was inhibited by simultaneous treatment with an anti-NRG-1β-neutralizing antibody ("anti-NRG"). All images are representative of at least 3 biological replicates.

FIG. 4A illustrates the protocols used to generate hESC-CMs under control or NRG-1/ErbB manipulated conditions. AA=activin A. FIG. 4B shows the percentage of cardiomyocytes exhibiting the nodal AP phenotype in hESC-CM cultures treated with control, non-immune IgG (25 mg/ml, n=33 cells), DMSO vehicle (0.1%, n=24 cells), anti-NRG-1β neutralizing antibody (25 mg/ml, n=38 cells), ErbB receptor antagonist AG1478 (10 mM, n=21 cells), or exogenous NRG-1β agonist (100 ng/ml) during day 5 to 12 (n=28 cells) or continuously after day 5 (n=21 cells). Note that interference with NRG-1/ErbB signaling greatly enhanced the proportion of nodal cells relative to control or NRG-1α treated conditions. In FIG. 4C, the preceding experiment was repeated using cGATA6-EGFP-transduced cultures, and plotted are the percentage of EGFP+ putative nodal cells generated under control or NRG-1/ErbB manipulated conditions (n=4 biological replicates). Note that, when corrected for the ~50% transduction efficiency, the proportion of nodal cells under each condition approximates that previously determined by direct AP phenotyping. Groups were compared by Fisher's exact test with Bonferroni correction. *P<0.05, **P<0.01.

In FIG. 6B, a differential interference contrast (DIC) picture combined with the fluorescence of EGFP (left panel) and the image stained with β-myosin heavy chain (β-MHC, right panel) from the same cells shows that all EGFP+ cells are cardiomyocytes. Scalebar=20 μm.

DETAILED DESCRIPTION OF THE INVENTION

Figure 1A:
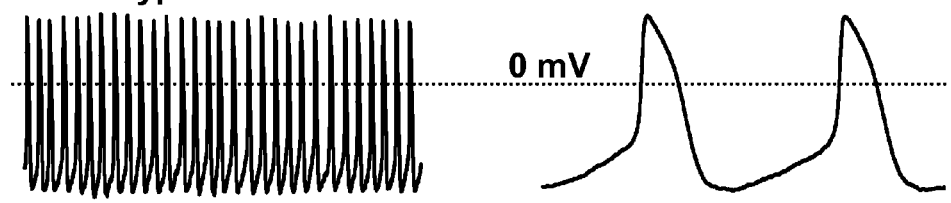
FIGS. 1A-1B show hESC-derived cardiomyocytes exhibit distinct nodal and working-type action potentials. Spontaneous action potentials ("APs") exhibited by two representative hESC-CMs showing characteristic nodal—(FIG. 1A) and working-type (FIG. 1B) AP waveforms and parameters. AP recordings were obtained from isolated cardiomyocytes at 36±1° C., using the perforated-patch clamp technique.

A first aspect of the present invention is directed to a method of producing cardiomyocytes having a nodal/pacemaker phenotype. This method involves culturing stem cells under conditions effective to produce cardiomyocytes and contacting the cardiomyocytes with an antagonist of neuregulin-1 or an antagonist of ErbB under conditions effective to induce the production of cardiomyocytes having a nodal/pacemaker phenotype In accordance with this aspect of the present invention, "stem cells" encompass cells which have the ability to proliferate and form cells of more than one different phenotype, and are further capable of self renewal, either as part of the same culture or when cultured under different conditions. Stem cells suitable for use in the methods of the present invention include embryonic stem cells or germ cells, adult stem cells, and induced pluripotent stem cells.

Embryonic stem ("ES") cells include any multi- or pluripotent stem cell derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art accepted test (e.g., the ability to form a teratoma in 8-12 week old SCID mice). In a preferred embodiment of the present invention, the stem cells are mammalian embryonic stem cells. More preferably, the embryonic stem cells of the present invention are human embryonic stem cells.

Methods for culturing embryonic stems cells, particularly human embryonic stem cells, are known in the art and described in WO2006/029297, WO2006/019366 and WO2006/029198 all to Thomson and Ludwig, and WO2008/089351 to Bergendahl and Thomson, which are hereby incorporated by reference in their entirety.

Embryonic germ ("EG") cells are derived from primordial germ cells and exhibit an embryonic pluripotent cell phenotype. EG cells are capable of differentiation into cells of ectodermal, endodermal, and mesodermal germ layers. EG cells can also be characterized by the presence or absence of markers associated with specific epitope sites. Methods for isolating, culturing, and characterizing human EG cells are described in Shamblott et al., "Human Embryonic Germ Cell Derivatives Express a Broad Range of Developmentally Distinct Markers and Proliferate Extensively In Vitro," *Proc Natl Acad Sci* 98(1):113-118 (2001), which is hereby incorporated by reference in its entirety.

Adult stem cells, as used in accordance with the present invention, encompass cells that are derived from any adult tissue or organ that replicate as undifferentiated cells and have the potential to differentiate into at least one, preferably multiple, cell lineages. General methods for producing and culturing populations of adult stem cells suitable for use in the present invention are described in WO2006/110806 to Xu et al., WO2002/057430 to Escoms et al., and WO2006/112365 to Nagaya, which are hereby incorporated by reference in their entirety. Cardiac progenitor or adult stem cells are particularly suitable for use in the present invention. Methods for isolating and culturing cardiac stem cells are described in WO2007/100530, WO2002/009650, and WO2002/013760 all to Anversa; WO2004/019767 to Schneider; and WO2006/052925 to Marban et al., which are all hereby incorporated by reference in their entirety.

Induced pluripotent stem cells ("iPSC") are also suitable for use in the methods of the present invention. iPSCs, as used herein, refer to pluripotent stem cells induced from somatic cells, e.g., a population of differentiated somatic cells (Takahashi et al., "Induction of Pluripotent Stem Cells From Adult Human Fibroblasts By Defined Factors," *Cell* 131(5):861-872 (2007); Park et al., "Reprogramming of Human Somatic Cells to Pluripotency With Defined Factors," *Nature* (2007); and Yu et al., "Induced Pluripotent Stem Cell Lines Derived From Human Somatic Cells," *Science* 318(5858):1917-1920 (2007), which are hereby incorporated by reference in their entirety). iPSCs are capable of self-renewal and differentiation into cell fate-committed stem cells, including various types of mature cells. iPSCs exhibit normal morphological (i.e., round shape, large nucleoli and scant cytoplasm) and growth properties, and express pluripotent cell-specific markers (e.g., Oct-4, SSEA-3, SSEA-4, Tra-1-60, Tra-1-81, but not SSEA-I). iPSCs are substantially genetically identical to their respective differentiated somatic cells of origin, yet display characteristics similar to higher potency cells, such as ES cells. iPSCs can be obtained from various differentiated (i.e., non-pluripotent and multipotent) somatic cells. Although various somatic cells are suitable for iPSC induction, higher reprogramming frequencies are observed when the starting somatic cells have a doubling time of about twenty-four hours. Somatic cells useful for carrying out the methods of the present invention include non-embryonic cells obtained from a fetal, newborn, juvenile or adult primates. Preferably, the somatic cells are human somatic cells. Examples of somatic cells include, but are not limited to, bone marrow cells, epithelial cells, fibroblast cells, hematopoietic cells, hepatic cells, intestinal cells, mesenchymal cells, myeloid precursor cells and spleen cells. Other somatic cells suitable for use in the present invention include CD29+ CD44+ CD166+ CD105+ CD73+ and CD31+ mesenchymal cells that attach to a substrate. Alternatively, the somatic cells can be cells that themselves proliferate and differentiate into other types of cells, including blood stem cells, muscle/bone stem cells, brain stem cells, and liver stem cells. Multipotent hematopoietic cells, including myeloid precursor or mesenchymal cells, are also suitable for use in the methods of the invention. Methods for producing and culturing populations of iPSCs are described in WO2008/118820 to Thomson and Yu and WO2007/069666 to Yamanaka, which are hereby incorporated by reference in their entirety.

In accordance with this aspect of the present invention, the stem cells are cultured under conditions effective to induce cardiomyocyte differentiation. As described herein, the preferred method for directing cardiomyocyte differentiation relies on sequential treatment of undifferentiated stem cells with activin-A and bone morphogenic protein-4 (BMP4) as described in WO2007/002136 and WO2005/090558 both to Gold et al.; WO2003/006950 to Xu; and Laflamme et al., "Cardiomyocytes Derived from Human Embryonic Stem Cells in Pro-Survival Factors Enhance Function of Infarcted Rat Hearts," *Nat Biotechnol* 25(9):1015-1024 (2007), which are hereby incorporated by reference in their entirety. This method reliably produces large quantities of relatively pure populations (~90%) of cardiomyocytes. The differentiated cardiomyocytes can be further contacted with a cocktail of pro-survival factors (e.g., Matrigel, Bcl-XL, cyclosporine A, a compound that opens ATP-dependent K+ channels, IGF-1, and the caspase inhibitor ZVAD-fmk) to limit cell death and promote survival upon transplantation to the target heart tissue.

Various other methods for directing cardiomyocyte differentiation that are known in the art are also suitable for use in the present invention (see e.g., WO2007/038933 to Rigshospitalet; WO2008/088882 to Bruneau and Takeuchi; WO2003/035838 to Epstein et al.; WO2004/081205 to Mummery et al.; WO2005/118784 to Mummery and Passier; WO2006/066320 to Passier and Mummery; and WO2007/070964 to Davidson et al., which are hereby incorporated by reference in their entirety).

Once a population of cardiomyocytes are obtained, inducing a nodal/pacemaker phenotype in these cells involves administering to the cardiomyocytes an antagonist of neuregulin-1 or an antagonist of ErbB. As used herein, "antagonist" broadly encompasses any agent that inhibits neuregulin-1 expression, activity, and/or signaling and any agent that inhibits ErbB receptor expression, activity, and/or signaling. The neuregulin-1 or ErbB antagonist of the present invention preferably inhibits neuregulin-1/ErbB mediated activity and signaling in the cardiomyocytes. In a preferred embodiment of the present invention, the antagonist of neuregulin-1 is an antagonist (i.e., inhibitor) of neuregulin-1β. Suitable antagonists of both neuregulin-1 and ErbB include nucleic acid molecule inhibitors, protein or peptide inhibitors, or small molecule inhibitors.

Suitable nucleic acid molecule inhibitors of neuregulin-1 and ErbB include antisense RNAs or RNAi, such as short interfering RNAs (siRNA), short hairpin RNAs (shRNA), microRNAs, and aptamers.

As described herein, methods of designing and making antisense RNA molecules, RNAi molecules, microRNAs and aptamers are well known in the art, and facilitated by knowledge of the nucleic acid sequence of the target molecule to be inhibited, in this case neuregulin-1 and/or ErbB. The nucleic acid sequence of human neuregulin-1 and its related isoforms have been described and are readily available to one of skill in the art (see Genbank Accession Nos. NM_004495.2 (neuregulin-1 isoform HRGγ); NM_013956.2 (neuregulin-1 isoform HRG-β1); NM_013957.2 (neuregulin-1 isoform HRG β2); NM_013958.2 (neuregulin-1 isoform HRG β3); NM_013959.2 (neuregulin-1 isoform SMDF); NM_013960.2 (neuregulin-1 isoform ndf43); NM_013961.2 (neuregulin-1 isoform GGF); NM_013962.2 (neuregulin-1 isoform GGF2); NM_013964.2 (neuregulin-1 isoform HRG-α), which are all hereby incorporated by reference in their entirety). Likewise, the nucleic acid sequences of the various human ErbB receptors are also known in the art (see Genbank Accession Nos. NM_004448 (ErbB2); NM_001982 (ErbB3); and NM_005235 (ErbB4), which are all hereby incorporated by reference in their entirety).

Methods of making antisense molecules and their use to inhibit the in vitro and in vivo translation of genes is well known in the art (see e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al.; U.S. Pat. No. 6,277,640 to Benett et al.; U.S. Pat. No. 6,255,111 to Bennett et al; and U.S. Patent Publication No. 20050130927 to Karl-Hermann et al., which are all hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see e.g., Weintraub H M, "Antisense RNA and DNA," *Scientific American* 262:40 (1990), which is hereby incorporated by reference in its entirety). The antisense nucleic acid molecules hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10-12 nucleotides in length, for example, at least 15, 20, 25, 50, 75, or 100 nucleotides in length. The antisense nucleic acid molecules can also be as long as the target nucleic acid with which it is intended to form an inhibitory duplex. In a preferred embodiment of the present invention, antisense molecules targeting neuregulin-1 inhibit or reduce the expression of neuregulin-1β. In another embodiment, antisense molecules targeting ErbB, inhibit or reduce the expression of ErbB2, ErbB3, ErbB4, or a combination thereof. Antisense molecules directed to human ErbB2 are described in U.S. Pat. No. 6,365,345 to Brysch et al.; U.S. Pat. No. 5,968,748 to Bennett et al.; and U.S. Patent Publication No. 20050130927 to Karl-Hermann et al., which are hereby incorporated by reference in their entirety. Antisense molecules directed to human ErbB3 and ErbB4 are described in U.S. Pat. Nos. 6,277,640 and 6,255,111, respectively, both to Bennett et al., which are hereby incorporated by reference in their entirety. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-22 nucleotides in length with short 2-3 nucleotide 3' overhangs on both ends. The double stranded siRNA molecule represents the sense and anti-sense strand of a portion of the target mRNA molecule, in this case a portion of the neuregulin-1 or ErbB mRNA sequence. siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. A number of exemplary siRNA molecules designed to target the human neuregulin-1 gene and isoforms thereof that are suitable for use in accordance with this aspect of the present invention are known in the art and are commercially available (e.g., Applied Biosystems, Foster City, Calif. and Abnova, Walnut, Calif.). Likewise, meroduplex RNA (mdRNA) molecules that interfere with neuregulin-1 gene expression via the cellular RNA interference machinery, are also useful in the methods of the present invention (WO2008/109555 to Quay et al., which is hereby incorporated by reference in its entirety).

siRNA molecules directed to the ErbB family of tyrosine kinase receptors are also well known in the art. In accordance with this aspect of the invention, an siRNA molecule that interferes with the expression of ErbB2, ErbB3, ErbB4, or any combination thereof is suitable for use. A number of exemplary siRNA molecules targeting Erb2 expression are described by Sahin et al., "Combinatorial RNAi for Quantitative Protein Network Analysis," *Proc Natl Acad Sci USA.* 104(16):6579-6584 (2007), which is hereby incorporated by reference in its entirety, including 5'-PCAUUGUGCAGAA-UUCGUCCUU (SEQ ID NO:1); 5'-PCCAUUGUGCA-GAAUUCGUCUU (SEQ ID NO:2); 5'-PAAACGUGUCU-GUGUUGUAGUU (SEQ ID NO:3); and 5'-PCAUCACGUAUGCUUCGUCUUU (SEQ ID NO:4). An exemplary diced-double stranded siRNA molecule directed to nucleotides 1038-1531 of the human ErbB3 gene sequence is described by Tapinos et al., "ErbB2 Receptor Tyrosine Kinase Signaling Mediates Early Demyelination Induced by Leprosy Bacilli," *Nat. Med.* 12(8):961-966 (2006), which is hereby incorporated by reference in its entirety. siRNA molecules targeting ErbB4 expression that can be used in accordance with this aspect of the present invention include 5'-ACUGAGCUCUCUCUCUGACTT-3' (SEQ ID NO:5) and 5'-GUCAGAGAGAGAGCUCAGUTT-3'(SEQ ID NO:6) (Maatta et al., "Proteolytic Cleavage and Phosphorylation of a Tumor-Associated ErbB4 Isoform Promote Ligand-Independent Survival and Cancer Cell Growth," *Mol Biol Cell.* 17(1):67-79 (2006), which is hereby incorporated by reference in its entirety).

Various modifications to the above referenced siRNA compositions, such as the incorporation of modified nucleosides or motifs into one or both strands of the siRNA molecule can be incorporated to enhance stability, specificity, and efficacy of the siRNA molecules. Such modifications are well known in the art and have been described in WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are all hereby incorporated by reference in their entirety.

Short or small hairpin RNA (shRNA) molecules are similar to siRNA molecules in function, but comprise longer RNA sequences that make a tight hairpin turn. shRNA is cleaved by cellular machinery into siRNA, and like siRNA, they silence gene expression via the cellular RNA interference pathway.

Nucleic acid aptamers are molecules that interact and bind to a target molecule (e.g., neuregulin-1β or ErbB) with a very high degree of specificity. Typically, aptamers are small nucleic acids ranging from 15-50 bases in length that fold into defined secondary and tertiary structures, such as stem-loops or G-quartets. Aptamers can bind small molecules as well as large molecules, as described in U.S. Pat. No. 5,631,146 to Szostak; U.S. Pat. No. 5,786,462 to Schneider; U.S. Pat. No. 5,543,293 to Schneider; and U.S. Pat. No. 5,580,737 to Polisky, which are all hereby incorporated by reference in their entirety. Aptamers can bind very tightly with $K_d$s for the target molecule of less than $10^{-12}$ M. It is preferred that the aptamers bind the target molecule with a $K_d$ less than $10^{-6}$. It is more preferred that the aptamers bind the target molecule with a $K_d$ less than $10^{-8}$.

Other nucleic acid molecules suitable for the inhibition of neuregulin-1 or ErbB include ribozymes (U.S. Pat. No. 5,334,711 to Sproat et al; U.S. Pat. No. 5,646,031 to DeYoung et al.; U.S. Pat. No. 5,595,873 to Joyce et al.; U.S. Pat. No. 5,580,967 to Joyce et al., which are hereby incorporated by reference in their entirety), triplex forming functional nucleic acid molecules (U.S. Pat. No. 5,176,996 to Hogan et al., which is hereby incorporated by reference in its entirety) or external guide sequences (EGSs) (WO 92/03566 to Yale, which is hereby incorporated by reference in its entirety).

Protein or peptide antagonists of neuregulin-1 and ErbB expression or activity are also suitable for use in accordance with this aspect of the present invention. Suitable protein inhibitors include, but are not limited to, antibodies (e.g. single chain antibodies, chimeric antibodies, hybrid antibodies), intrabodies, peptabodies, peptide aptamers, or any other binding molecules, including synthetic peptide inhibitors, having antigen binding specificity for neuregulin-1 or ErbB. The amino acid sequences encoding the human neuregulin-1 protein and its isoforms and the various ErbB receptor tyrosine kinases are known in the art (see NCBI Protein Accession Nos. NP_004486 (neuregulin-1 isoform HRG-γ); NP_039250.2 (neuregulin-1 isoform HRGβ1); NP_039251.2 (neuregulin-1 isoform HRG-β2); NP_039252.2 (neuregulin-1 isoform HRG-β3); NP_039253.1 (neuregulin-1 isoform SMDF); NP_039254.1 (neuregulin-1 isoform ndf43); NP_039255.1 (neuregulin-1 isoform GGF); NP_039256.2 (neuregulin-1 isoform GGF2); NP_039258.1 (neuregulin-1 isoform HRG-α); NP_00439.2 (human ErbB2); NP_001973.2 (human ErbB3); NP_005226.1 (human ErbB4), which are all hereby incorporated by reference in their entirety), and, therefore, facilitate the generation of new protein or peptide antagonists using standard techniques known in the art.

Preferred antibodies or other inhibitory binding molecules of the present invention are those having antigen specificity for neuregulin-1 or ErbB, where upon binding of the antibody or binding molecule to neuregulin-1 or ErbB the expression and/or activity of neuregulin-1 or ErbB is inhibited or significantly reduced. Antibodies of the present invention include monoclonal antibodies (including full length monoclonal antibodies), polyclonal antibodies, multispecific antibodies (e.g., bispecific antibodies), intrabodies, peptabodies, and antibody fragments. Antibody fragments comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

Antibodies having antigen specificity for neuregulin-1 are known in the art (see e.g. Trinidad et al., "The Agrin/MuSK Signaling Pathway is Spatially Segregated from the Neuregulin/ErbB Receptor Signaling Pathway at the Neuromuscular Junction," *J Neuroscience* 20(23):8762-70 (2000), which is hereby incorporated by reference in its entirety) and are commercially available (e.g., Genetex, San Antonio, Tex.; R&D Systems, Minneapolis, Minn.; Abnova, Walnut, Calif.). In a preferred embodiment of the present invention, the neuregulin-1 antibody is a neutralizing antibody as described herein in the Examples.

Antibodies having antigen specificity to ErbB are also well known in the art (see e.g., Gilmour et al., "Neuregulin Expression, Function, and Signaling in Human Ovarian Cancer Cells," *Clin Cancer Res.* 8(12):3933-3942 (2002) (anti-ErbB3 antibody); Labriola et al., "Heregulin Induces Transcriptional Activation of the Progesterone Receptor by a Mechanism that Requires Functional ErbB-2 and Mitogen-Activated Protein Kinase Activation in Breast Cancer Cells," *Mol Cell Biol.* 23(3):1095-1111 (2003) (anti-Erb4 antibody); Grim et al., "ErbB-2 Knockout Employing an Intracellular Single-Chain Antibody (sFv) Accomplishes Specific Cytotoxicity in ErbB-2 Expressing Lung Cancer Cells," *Am J Resp Cell Mol Biol* 15:348-354 (1996) (ErbB-2 single-chain antibody), U.S. Pat. No. 5,821,337 to Carter et al. (humanized ErbB-2 antibody Herceptin); and U.S. Patent Publication No. 20060233808 to Deperthes (peptabodies to ErbB-1, -3, and -4), which are all hereby incorporated by reference in their entirety). Anti-ErbB antibodies are also commercially available (e.g., Neomarkers/Lab Visions, Fremont, Calif.). Alternatively, polyclonal or monoclonal antibodies directed to human neuregulin-1 or ErbB can be obtained using standard techniques and procedures known in the art for generating antibodies (see e.g., ANTIBODIES: A LABORATORY MANUAL (Edward Harlow & David Lane eds., Cold Spring Harbor Laboratory, 1988) and LAWRENCE B. SHOOK, MONOCLONAL ANTIBODY PRODUCTION TECHNIQUES AND APPLICATIONS, 51-63 (1987), which are hereby incorporated by reference in their entirety).

Other antibodies or protein or peptide binding molecules useful for carrying out the methods of the present invention include those having antigen binding specificity for a protein in the neuregulin-1 or ErbB signal transduction pathway, where upon binding of the antibody or other binding molecule to its target protein, neuregulin-1 or ErbB function is indirectly disrupted.

Alternative protein inhibitors suitable for use in this aspect of the present invention include dominant negative forms of the neuregulin-1 or ErbB proteins. U.S. Patent Application Publication No. 20050123538 to Shemesh et al., which is hereby incorporated by reference in its entirety, describes dominant negative forms of human ErbB2 which are devoid of transmembrane and intracellular kinase domains, yet retain their ability to dimerize with other ErB receptors. These dominant negative forms of ErbB2 sequester ErbB1, ErbB3, and ErbB4 proteins, thereby inhibiting their biological activity. Other peptide ligands, including both linear and cyclic peptide ligands that bind to and inhibit ErbB are described in U.S. Pat. No. 6,987,088 to Dennis, which is hereby incorporated by reference in its entirety.

Other protein or peptide inhibitors of ErbB that are suitable for use in the methods of the present invention include recombinant proteins or peptide fragments thereof which mimic endogenous negative regulators of ErbB. For example, c-cbl and Nrdp1 are ubiquitin ligases which control ErbB receptor degradation (Levkowitz et al., "Ubiquitin Ligase Activity and Tyrosine Phosphorylation Underlie Suppression or Growth Factor Signaling by c-Cble/Sli-1," *Mol Cell* 4:1029-40 (1999); Diamonte et al., "An RBCC Protein Implicated in Maintenance of Steady-State Neuregulin Receptor Levels," *Proc Natl Acad Sci USA* 99:2866-2871 (2002); and Qiu et al., "Nrdp1/FLRF is a Ubiquitin Ligase Promoting Ubiquitination and Degradation of the Epidermal Growth Factor Receptor Family member, ErbB3," *Proc Natl Acad Sci USA* 99:14843-48 (2002), which are hereby incorporated by reference in their entirety). Recombinant c-cbl or Nrdp1 proteins or peptide fragments, or nucleic acid molecules encoding such recombinant proteins or peptides, can be utilized to enhance ErbB receptor degradation thereby downregulating its activity. The nucleic acid and amino acid sequences of c-cbl (GenBank Accession No. CAA40393, which is hereby incorporated by reference in its entirety) and Nrdp1 (NCBI Ref Seq Nos. NP_005776 and NM_005785, which are hereby incorporated by reference in it entirety) are well known in the art. Likewise, recombinant proteins or peptide fragments thereof, or nucleic acid molecules encoding the recombinant proteins or peptide, mimicking the ErbB negative modulator proteins, herstatin, Argos, CPI, and Kek1 (Azios et al., "Expression of Herstatin, an autoinhibitor of HER-2/neu, Inhibits Transactivation of Her-3 by Her-2 and Blocks EGF Activation of the EGF Receptor," *Oncogene* 20:5199-5209 (2001); Blanco-Aparicio et al., "Potato Carboxypeptidase Inhibitor, a T-Knot Protein, is an Epidermal Growth Factor Antagonist that Inhibits Tumor Cell Growth," *J Biol Chem* 273:12370-12377 (1998); Ghiglione et al., "Mechanism of Inhibition of the Drosophila and Mammalian EGF Receptors by the Transmembrane Protein Kekkon-1," *Development* 130:4483-4493 (2003); Sweeny et al., "Negative Regulation of ErbB Family Receptor Tyrosine Kinases," *British J Cancer* 90:289-93 (2004), which are all hereby incorporated by reference in their entirety), are also suitable for inhibiting ErbB mediated activity in accordance with the methods of the present invention. The nucleic acid and amino acid sequence of human herstatin is well known in the art (GenBank Accession No. AAD56009, which is incorporated by reference in its entirety).

Small molecule inhibitors suitable for use in accordance with this aspect of the present invention include the pan-ErbB small molecule inhibitors, JNJ-28871063 (Emanuel et al., "Cellular and In Vivo Activity of JNJ-28871063, a Non-quinazoline Pan-ErbB Kinase Inhibitor that Crosses the Blood-Brain Barrier and Displays Efficacy Against Intracranial Tumors," *Mol Pharmacol.* 73(2):338-348 (2008), which is hereby incorporated by reference in its entirety) and CI-1033 (Slichenmyer et al., "CI-1033, a Pan-ErbB Tyrosine Kinase Inhibitor," *Semin Oncol.* 28(5 Suppl 16):80-85 (2001), which is hereby incorporated by reference in its entirety). Likewise, the ErbB1/ErbB2 small molecule inhibitor PKI166 (Brandt et al., "Mammary Glands Reconstituted with Neu/ErbB2 Transformed HC11 Cells Provide a Novel Orthotopic Tumor Model for Testing Anti-Cancer Agents," *Oncogene* 20(39):5459-5465 (2001), which is hereby incorporated by reference in its entirety) is also suitable for use. Other small molecule inhibitors of ErbB that can be used in the methods of the present invention include, tryphostin AG825, AG1478, PD158780, and BIBX1382B2 (see e.g., Egeblad et al., "BIBX1382BS, but Not AG1478 or PD153035, Inhibits the ErbB Kinases at Different Concentrations in Intact Cells," *Biochem Biophys Res Commun* 281 (1):25-21 (2001), which is hereby incorporated by reference in its entirety).

Another aspect of the present invention relates to an isolated population of nodal/pacemaker cardiomyocytes. In a preferred embodiment, the isolated population of nodal/pacemaker cardiomyocytes are human nodal/pacemaker cardiomyocytes derived from human stem cells in accordance with the methods described herein. This isolated population of human nodal/pacemaker cardiomyocytes is characterized by unambiguous molecular and electrophysiological markers. Electrophysiological markers include a spontaneous firing rate of >90 bpm (mean of 122 bpm); a slow, biphasic action potential upstroke (dV/dtmax<15 V/s, mean of 6.5 V/s); robust pacemaker current under voltage clamp; and comparatively little opposing IK1 current (see Table 1 below, all parameters acquired at 37° C.). Importantly, because these cells are true pacemaker/nodal cardiomyocytes, these cells retain the aforementioned electrophysiological characteristics with maturation. The human pacemaker/nodal cardiomyocytes also exhibit immunophenotypic markers including the usual pan-cardiac proteins (i.e., sarcomeric actin, sarcomeric myosin, troponins) as well the pacemaker channel HCN4 protein expression. Finally, the isolated population of nodal/pacemaker cardiomyocytes of the present invention have reduced expression of "working" (i.e., atrial or ventricular chamber-specific) cardiac markers including KCNJ2 (ion channel gene underlying IK1), SCN5A, and MLC2v.

pacemaker cardiomyocytes of the present invention and delivering the isolated population of nodal/pacemaker cardiomyocytes to the subject under conditions effective to treat the cardiac arrhythmia.

In a preferred embodiment of this aspect of the present invention, a subject having a cardiac arrhythmia is selected and the isolated population of nodal/pacemaker cardiomyocytes is delivered to this selected subject. The selected subject may have any type of cardiac arrhythmia condition, including, but not limited to, sinus node dysfunction (e.g. "sick sinus" syndrome), bifascicular block, trifascicular block, third-degree atrial-ventricular block, Stokes-Adam attack, or atrial fibrillation. The selected subject can be any animal, preferably a mammal, having a cardiac arrhythmia. In a preferred embodiment of the present invention, the selected subject is a human subject.

Preferably, the isolated population of nodal/pacemaker cardiomyocytes are made in accordance with the methods of

TABLE 1

Characteristics of Nodal/Pacemaker and Atrial/Ventricular ("Working") Cardiomyocytes

|  | N | $dV/dt_{max}$ (V/s) | $APD_{50}$ (ms) | APA (mV) | MDP (mV) | Rate (bpm) |
| --- | --- | --- | --- | --- | --- | --- |
| Nodal-like CMs | 14 | 6.5 ± 4.1** | 104.3 ± 26.4* | 74.9 ± 11.2** | −47.2 ± 4.6** | 122.0 ± 36.5* |
| Working CMs | 31 | 44.2 ± 31.7 | 144.7 ± 48.9 | 96.8 ± 14.9 | −57.5 ± 8.9 | 85.8 ± 29.0 |

Data are mean ± SD. Abbreviations are as follows:
N = cell number,
$APD_{50}$ = action potential duration measured at 50% repolarization,
$dV/dt_{max}$ = maximum rate of action potential upstroke,
APA = action potential amplitude,
MDP = maximum diastolic potential.
**P < 0.01 and *P < 0.001 nodal-like vs. working CMs.

Another aspect of the present invention is directed to a pharmaceutical composition comprising the nodal/pacemaker cardiomyocytes produced in accordance with the methods of the present invention. In a preferred embodiment, the nodal/pacemaker cardiomyocytes of the pharmaceutical composition are human nodal/pacemaker cardiomyocytes, and are produced in accordance with the methods of producing nodal/pacemaker cardiomyocytes described supra. The pharmaceutical composition further includes a pharmaceutically acceptable carrier, such as an isotonic excipient prepared under sufficiently sterile conditions for human administration. For general principles in medicinal formulation see CELL THERAPY: STEM CELL TRANSPLANTATION, GENE THERAPY, AND CELLULAR IMMUNOTHERAPY (George Morstyn & William Sheridan eds., Cambridge University Press, 1996) and EDWARD D. BALL et al., HEMATOPOIETIC STEM CELL THERAPY (Churchill Livingstone, 2000).

Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocytes upon implantation. Suitable ingredients include matrix proteins that support or promote adhesion of the cardiomyocytes, or complementary cell types, especially endothelial cells. Additional ingredients that may be included to promote survival of cardiomyocytes upon deliver include Matrigel, a Bcl-XL peptide, cyclosporine A, a compound that opens ATP-dependent K+ channels, IGF-1, and a caspase inhibitor.

Another aspect of the present invention is directed to a method of treating cardiac arrhythmia in a subject. This method involves providing an isolated population of nodal/ the present invention. Appropriate methods and reagents for inducing cardiomyocyte differentiation and producing cardiomyocytes having a nodal/pacemaker phenotype are described supra.

In accordance with this aspect of the present invention, the cardiomyocytes having a nodal/pacemaker phenotype can be delivered to subject having the arrhythmia via means known in the art, including a catheter-based or direct intramyocardial injection during surgery. In a preferred embodiment of the present invention, the nodal/pacemaker cells are delivered by catheter guided by simultaneous or previous electroanatomic mapping procedures (e.g., the NOGA system) which are used to diagnose, localize, and treat certain cardiac rhythm disturbances. These methods are known in the art, see e.g., Perin et al., "Stem Cell Therapy in End-Stage Ischaemic Heart Failure: A Catheter-Based Therapeutic Strategy Targeting Myocardial Viability," *Euro. Heart J.* 8(Suppl. H):H46-H51 (2006) and Psaltis et al., "Intramyocardial Navigation and Mapping for Stem Cell Delivery," *J of Cardiovasc. Trans. Res.* DOI 10.1007/s12265-009-9138-1 (2009), which are hereby incorporated by reference in their entirety). In another embodiment of the present invention, magnetic resonance (MR) guided intramyocardial delivery of the nodal/pacemaker cardiomyocytes, as described by Karmarkar et al., "MR-Trackable Intramyocardial Injection Catheter," *Magnetic Resonance in Medicine* 51(6):1163-72 (2004), which is hereby incorporated by reference in its entirety, is used for delivering cells to the desired location in the heart (i.e., the native SA node or AV node structures or elsewhere in the conduction system).

While a catheter-based approach for delivering the pacemaker cells to a subject are superior, these cells can also be delivered directly by intramuscular injection via thoracotomy (e.g., by the surgeon during coronary bypass grafting). Other alternatives to catheter-based delivery include intracoronary infusion, intravenous injection, bolus injection via a catheter during a surgical procedure such as a percutaneous transluminal coronary angioplasty, transendocardial injection, transvascular injection, intramuscular injection, or intra-arterial injection.

One or more injections, infusions, or implantations of cardiomyocytes may be necessary to provide pacemaker activity in larger mammals such as humans. Anticipated total graft sizes in humans are from about $2.5 \times 10^4$ to $1 \times 10^8$ cells or more. These established, viable grafted cells can be provided by one or multiple cellular implantations, e.g., by implanting up to about $10^8$ or more cells at a time. In a preferred embodiment cardiomyocytes are delivered to the target heart tissue multiple times, delivering up to about $2.5 \times 10^4$ to $1 \times 10^8$ cells at a time to add to the size of the graft and optimize its biological pacing or other activity.

The cardiomyocytes of the present invention are administered in a manner that permits them to graft or migrate to the intended tissue site and reconstitute or regenerate the functionally deficient area. To reduce the risk of cell death upon engraftment, the cells may be treated by heat shock or cultured with 0.5 U/mL erythropoietin 24 hours before administration. Where desirable, the patient receiving an allograft of cardiomyocytes can be treated to reduce immune rejection of the transplanted cells. Methods contemplated include the administration of traditional immunosuppressive drugs like cyclosporin A (Dunn et al., "Cyclosporin: An Updated Review of the Pharmacokinetic Properties, Clinical Efficacy and Tolerability of a Microemulsion-Based Formulation (neoral)1 in Organ Transplantation," *Drugs* 61:1957 (2001), which is hereby incorporated by reference in its entirety), or inducing immunotolerance (see e.g., WO2002/44343 to Chiu et al.; WO2003/050251 to Bhatia et al.; and U.S. Pat. No. 6,280,718 to Kaufman, which are hereby incorporated by reference in their entirety). Another approach is to adapt the cardiomyocyte cell population to decrease the amount of uric acid produced by the cells upon transplantation into a subject, for example, by treating them with allopurinol. Alternatively or in conjunction, the individual is prepared by administering allopurinol, or an enzyme that metabolizes uric acid, such as urate oxidase (see e.g., WO2005/06630 to Gold, which is hereby incorporated by reference in its entirety).

Another aspect of the present invention is directed to a method of producing cardiomyocytes having an atrial/ventricular phenotype. This method involves culturing stem cells under conditions effective to produce cardiomyocytes and contacting the cardiomyocytes with a neuregulin-1 agonist, neuregulin-1 mimetic, or a related agonist of an ErbB receptor under conditions effective to induce the production of cardiomyocytes having an atrial/ventricular phenotype.

Cardiomyocytes having an atrial/ventricular phenotype, also referred to as a "working" phenotype are the reciprocal of nodal cardiomyocytes. The unique electrophysiological and molecular characteristics of atrial/ventricular cells produced in accordance with the methods of the present invention are described in more detail below and are listed in Table 1 above.

Appropriate stem cells and reagents for producing differentiated cardiomyocytes suitable for use in this aspect of the invention are described supra.

In accordance with this aspect of the invention, production of cardiomyocytes having an atrial/ventricular phenotype involves culturing cardiomyocytes with a neuregulin-1 agonist, neuregulin-1 mimetics, or related agonists of the corresponding ErbB receptors (ErbB2, ErbB3, and ErbB4). Suitable agonists of both neuregulin-1 and ErbB include recombinant protein or peptide fragments of neuregulin-1 or other ErbB receptor ligands and the nucleic acid molecules encoding the same, antibody agonists, and small molecule agonists.

Recombinant protein or peptide fragments of neuregulin suitable for use in the present invention include any neuregulin protein or peptide that can bind to and activate ErbB2, ErbB3, ErbB4 or combinations thereof, including but not limited to any of the neuregulin isoforms (Genbank and protein accession numbers for neuregulin-1 are described supra), polypeptides comprising the neuregulin epidermal growth factor-like (EGF) domain alone, polypeptides containing the neuregulin EGF-like domain, neuregulin mutants or derivatives, and any kind of neuregulin-like gene product that encodes the aforementioned protein and peptide fragments that activate the ErbB receptors. In a preferred embodiment, the neuregulin protein or peptide fragments of the present invention are human neuregulin-1β protein or peptide fragments.

As discussed supra, recombinant neuregulin peptides consisting of the EGF-like domain alone are sufficient to activate the appropriate ErbB receptors. As used herein, "EGF-like domain" refers to a polypeptide motif encoded by the neuregulin gene that binds to and activates ErbB2, ErbB3, ErbB4, or combinations thereof, and bears a structural similarity to the epidermal growth factor receptor-binding domain (see e.g., Buonanno & Fischbach, "Neuregulin and ErbB Receptor Signaling Pathways in the Nervous System," *Curr Opin Neurobiol* 11:287-96 (2001) (showing alignment of the human EGF-like domains in neuregulins 1-4 and other EGF related ligands), which is hereby incorporated by reference in its entirety). Exemplary recombinant peptides containing the neuregulin EGF-like domain that are known to activate ErbB signaling are disclosed in WO2000/64400 to Marchionni et al.; WO1997/09425 to Chang; WO2000/037095 to Zhou et al.; and WO2003/020911 to Stefansson et al., which are hereby incorporated by reference in their entirety.

Suitable ErbB agonists for use in accordance with this aspect of the present invention include the recombinant neuregulin protein and peptide fragments discussed supra. In addition, ErbB receptor ligands or ligand fragments other than neuregulin that bind to and activate ErbB including heregulin, amphiregulin, betacellulin, and epiregulin, are also suitable for purposes of the present invention. Recombinant heregulin, amphiregulin, betacellulin, and epiregulin ErbB receptor ligands, or active peptide fragments thereof, are disclosed in U.S. Patent Publication Nos. 20010007657 to Reid et al.; 20080031880 to Huang et al.; 20070054851 to Lin et al.; and U.S. Pat. No. 6,136,558 to Ballinger et al., which are all hereby incorporated by reference in their entirety.

In another embodiment of the present invention, the agonist of ErbB is an ErbB receptor agonist antibody (see e.g., U.S. Patent Publication No. 20080031880 to Huang et al., and Amin et al., "Gene Expression Profiling of ErbB Receptor and Ligand-Dependent Transcription," *Oncogene* 23:1428-38 (2004), which are hereby incorporated by reference in their entirety).

Another aspect of the present invention is directed to an isolated population of atrial/ventricular cardiomyocytes. In a preferred embodiment, the isolated population of atrial/ventricular cardiomyocytes are human atrial/ventricular cardiomyocytes produced in accordance with the methods of the present invention described herein. The isolated population of human atrial/ventricular cardiomyocytes of the present invention are characterized by electrophysiological characteristics including a slower spontaneous firing rate (mean of ≅85 bpm), a very rapid action potential upstroke (>>15 V/s, mean of 45 V/s), a longer action potential duration, and substantial fast sodium current (See Table 1, above). Correspondingly, these cells show strong expression of the ion channel genes SCN5A and KCNJ2 and reduced expression of the HCN pacemaker family genes. The atrial/ventricular cells of the present invention express usual pan-cardiac markers (sarcomeric actin, sarcomeric myosin, troponins) and strongly express working/chamber-specific markers appropriate for developmental stage (e.g., MLC2v, atrial natriuretic factor). These cells retain these phenotype markers with maturation; moreover, unlike pacemaker cells, working cardiomyocytes should hypertrophy and show increased single-cell force generation with development.

Another aspect of the present invention is directed to a pharmaceutical composition containing the atrial/ventricular cardiomyocytes of the present invention. In a preferred embodiment, the pharmaceutical composition contains an isolated population of human atrial/ventricular cardiomyocytes. The pharmaceutical composition further contains a pharmaceutically acceptable carrier and additional ingredients that facilitate engraftment and mobilization upon implantation as described supra for the composition containing the nodal/pacemaker cardiomyocytes. In a preferred embodiment, the isolated population of human atrial/ventricular cardiomyocytes are produced in accordance with the methods described supra.

Another aspect of the present invention is directed to a method of improving cardiac tissue repair or cardiac organ function in a subject. This method involves providing an isolated population of atrial/ventricular cardiomyocytes and delivering the isolated population of atrial/ventricular cardiomyocytes to the subject under conditions effective to improve cardiac tissue repair or cardiac organ function.

In a preferred embodiment of the present invention, the isolated population of atrial/ventricular cardiomyocytes are produced in accordance with the methods of the present invention. Appropriate methods and reagents for inducing cardiomyocytes differentiation and producing cardiomyocytes having an atrial/ventricular phenotypes are described supra.

In accordance with this aspect of the present invention a subject in need of cardiac tissue repair or improved cardiac organ function is first selected and the isolated population of atrial/ventricular cardiomyocytes are delivered to the selected subject. Individuals in need of cardiac tissue repair or improved cardiac organ function who are suitable for receiving cardiomyocyte based therapy include those suffering from or having suffered from congestive heart failure, myocardial infarction, coronary heart disease, cardiomyopathy, endocarditis, congenital cardiovascular defects, and congestive heart failure, or any condition resulting in cardiac tissue injury (e.g., ischemia, apoxia, hypoxia, etc.)

Methods of delivering the cardiomyocytes having atrial/ventricular phenotypes include catheter-based or direct intramyocardial injection and intracoronary infusion as described supra. In accordance with this aspect of the present invention, the cardiomyocytes having atrial/ventricular phenotypes can be delivered as a composition which includes a biocompatible scaffold to further facilitate tissue regeneration (See WO2005/095652 to Ebert et al., which is hereby incorporated by reference in its entirety).

In a preferred embodiment of this aspect of the present invention, the cardiomyocytes will be delivered to the region of, or adjacent to the region of injured myocardium, and will be introduced as soon as possible after the infarct or other injury. Preferably, the cardiomyocytes are delivered during active granulation tissue formation but prior to scarring and myocardial thinning. Preferably, the delivered cardiomyocyte cells are physically and electronically coupled to the viable native myocardium adjacent to the injured myocardium. Such coupling can be observed, for example, by the organization of the engrafted cells and the formation of nascent junctional complexes both between engrafted cells themselves and between engrafted cells and the native cardiomyocytes. Several implantations of cardiomyocytes may be necessary to provide the restorative tissue properties. These may be provided, for example, by one or more infusions, implantations, or infusions of cells, with each delivery having up to about $1 \times 10^6$ to $1 \times 10^9$ cells or more. In a preferred method, multiple cellular administrations (e.g., injections) of $2.5 \times 10^5$ to $2.5 \times 10^6$ cells at a time to achieve an appropriate graft size of $1 \times 10^7$ to $1 \times 10^9$ cells. At least one implantation of cells will be made such that the engrafted cells contact viable myocardial tissue on the perimeter of the injured region of myocardium. Where a larger region of injury is involved, multiple injections or implantations of cells may be made around the periphery of the injured region so as to substantially surround the injured region with engrafted, viable cells. Furthermore, in subsequent implantations conducted in the same operative procedure or in follow-up procedures, cells from a prior engraftment may be used as the newly established periphery, and grafts may be constructed so as to provide viable, coupled cardiomyocytes substantially into or substantially throughout the injured myocardial region, so as to provide the improved functionality to the region. After one or multiple procedures for restorative engraftment, the individual can be monitored for improvement in contractile function of the heart and the loss or decrease in functional artifacts caused by the injured region of myocardium. Such monitoring can be conducted by signal processing methodologies which are known and used in the detection and localization of ischemic or other injured myocardium. The efficacy of cellular delivery treatment can also be monitored by the reduction in area occupied by scar tissue or revascularization of scar tissue, and in the frequency and severity of angina; or an improvement in developed pressure, systolic pressure, end diastolic pressure, $\Delta$pressure/$\Delta$time, patient mobility, and quality of life.

The present invention is illustrated, but not limited, by the following examples.

EXAMPLES

Example 1

Generation and Characterization of hESC-CMs

H7 human embryonic stem cells (H7 hESCs) were maintained in an undifferentiated state on Matrigel (BD Biosciences) coated plates in mouse embryonic fibroblast conditioned medium (MEF-CM) supplemented with 4 ng/ml bFGF (Peprotech), as previously described (Xu et al., "Feeder-Free Growth of Undifferentiated Human Embryonic Stem Cells," *Nat. Biotechnol.* 19(10):971-974 (2001), which is hereby incorporated by reference in its entirety). H7 hESCs were induced to differentiate into cardiomyocytes by the sequential application of 100 ng/ml activin for 24 hours followed by 4 days of 10 ng/ml BMP4. After 1 week in RPMI/B27 without added growth factors, cells were dispersed using Blendzyme 4 (Roche) and plated overnight onto glass-bottom Petri dishes, using medium containing 20% fetal calf serum (Hyclone). On the following day, the medium was returned to serum-free medium and cells were cultured for an additional 7-27 days. The spontaneously generated action potentials of hESC-derived cardiomyocytes at 35-36° were then recorded using a HEKA EPC-10 amplifier (which has a true "voltage follower" circuit, similar to a classical microelectrode amplifier), controlled by a Dell Optiplex GX280 SMT Pentium 4 computer and operated in current clamp mode. After obtaining gigaohm seal, electrical access to the cells was obtained via the β-escin perforated patch technique. The capacitance of the examined cells was 17.5±7.6 pF (range 5.8-32.8 pF), in comparison to the ~150 pF typically reported for adult human ventricular myocytes. Bath medium was (in mM) 140 NaCl, 5.4 KCl, 1.8 $CaCl_2$, 1.0 $MgCl_2$, 0.33 $NaH_2PO_4$, 5 dextrose, and 10 HEPES, adjusted to pH 7.40 with NaOH. The pipette solution was (in mM) 135 KCl, 5 $Na_2$creatine phosphate, 5 MgATP and 10 HEPES, adjusted to pH 7.20 with KOH. Data were digitized at 10 kHz and filtered at 2 kHz. Action potential parameters were analyzed using Patchmaster (HEKA) and Igor Pro software.

Example 2

Reverse Transcription-Polymerase Chain Reaction (RT-PCR) Analysis

Total RNA was prepared by lysing cell preparations with the Qiagen RNEasy kit, followed by DNase treatment. After confirming the quality of the RNA using an Agilent Bioanalyzer 2100, it was reverse-transcribed into cDNA using the Superscript III first-strand cDNA synthesis kit (Invitrogen). Tables 2 and 3 list the primers used for semi-quantitative and quantitative RT-PCR reactions, respectively. All primer pairs were designed to be intron-spanning Quantitative real-time PCR reactions were performed using the SYBR green dye system and an Applied Biosystems 7900HT instrument. Cycling conditions were 10 minutes at 95° C., and 40 cycles of 30 seconds at 95° C., 30 seconds at 55° C., and 30 seconds at 72° C. mRNA levels were normalized using GAPDH as an internal control, and adult human heart cDNA was always run in parallel as a positive control.

TABLE 2

Primer Sets Used for Semi-Quantitative RT-PCR

| Gene | Forward Primer Sequence<br>Reverse Primer Sequence | Product Size (bp) | Annealing Temp (° C.) |
|---|---|---|---|
| RG-1α | TTGCTCCAGTGAATCCAGGTT<br>(SEQ ID NO: 7)<br>TGAAAAGCCAGGAATCGGCTG<br>(SEQ ID NO: 8) | 34 | 55 |
| RG-1β | CGATCACCAGTAAACTCATTTG<br>(SEQ ID NO: 9)<br>TGAAAAGCCAGGAATCGGCTG<br>(SEQ ID NO: 10) | 35 | 55 |
| rbB1 | GGCATAGGAATTTTCGTAGTACATAT<br>(SEQ ID NO: 11)<br>GACCCTCCGGGACGG<br>(SEQ ID NO: 12) | 50 | 60 |
| rbB2 | GGGGCTGGGGCAGCCGCTC<br>(SEQ ID NO: 13)<br>GGCTGCTGGACATTGACGAG<br>(SEQ ID NO: 14) | 31 | 60 |
| rbB3 | CAGGTCTGGCAAGTATGGAT<br>(SEQ ID NO: 15)<br>GGAGTACAAATTGCCAAGGGTA<br>(SEQ ID NO: 16) | 27 | 60 |
| rbB4 | CATTGTATTCTTTTTCATCTCCTTC<br>(SEQ ID NO: 17)<br>CTCTGATCATGGCAAGTATGGAT<br>(SEQ ID NO: 18) | 24 | 60 |
| β-actin | CAAGGCCAACCGCGAGAAGATGAC<br>(SEQ ID NO: 19)<br>AGGAAGGAAGGCTGGAAGAGTGC<br>(SEQ ID NO: 20) | 20 | 58 |

TABLE 3

Primer Sets Used for Quantitative RT-PCR Analysis

| Gene | Aliases (Associated Currents) | Accession ID | Forward Primer Sequence<br>Reverse Primer Sequence |
|---|---|---|---|
| CACNA1C | Cav1.2<br>($I_{CaL}$) | NM 000719 | CAGAGGCTACGATTTGAGGA<br>(SEQ ID NO: 21)<br>GCTTCACAAAGAGGTCGTGT<br>(SEQ ID NO: 22) |
| CANCA1G | Cav3.1<br>($I_{CaT}$) | NM 198397 | CTTCACACCATATGCTGTCT<br>(SEQ ID NO: 23)<br>CTGCTCCACCATGTAGCTCT<br>(SEQ ID NO: 24) |
| GJA1 | Cx43 | NM 000165 | CTTTTGGAGTGACCAGCAAC<br>(SEQ ID NO: 25)<br>TGAAGCTGAACATGACCGTA<br>(SEQ ID NO: 26) |
| GJA5 | Cx40 | NM 181703 | GCAGCCTCAGCTTTACAAATG<br>(SEQ ID NO: 27)<br>GTGACAGATGTTGGCAGGAAT<br>(SEQ ID NO: 28) |
| GJA7 | Cx45 | NM 005497 | TCTCACTCGCATCAGAATCA<br>(SEQ ID NO: 29) |

TABLE 3-continued

Primer Sets Used for Quantitative RT-PCR Analysis

| Gene | Aliases (Associated Currents) | Accession ID | Forward Primer Sequence Reverse Primer Sequence |
|---|---|---|---|
| | | | AAGAGCAAAGGACACACCAC (SEQ ID NO: 30) |
| HCN1 | ($I_f$) | NM 021072 | GTGACAGAAAGCAGGGGTAA (SEQ ID NO: 31) ATTGCCAGTGCCAGAGATAC (SEQ ID NO: 32) |
| HCN2 | ($I_f$) | NM 001194 | AGCTCAAGTTCGAGGTCTTCC (SEQ ID NO: 33) TCTCCTTGTTGCCCTTAGTGA (SEQ ID NO: 34) |
| HCN4 | ($I_f$) | NM 005477 | TGATGGTGGGAAACCTGATTA (SEQ ID NO: 35) GTTGAGGACCAAGTCGATGAG (SEQ ID NO: 36) |
| KCNE1 | mink, ISK ($I_{Ks}$) | NM 000219 | CAGGCCAGATTTACAGGAGA (SEQ ID NO: 37) GCAGAATCAGTGTGTGCTTG (SEQ ID NO: 38) |
| KCNE2 | MiRP1 ($I_{Kr}$, $I_f$, $I_{to}$) | NM 172201 | TCATGGTGATGATTGGAATG (SEQ ID NO: 39) TTATCAGGGGGACATTTTGA (SEQ ID NO: 40) |
| KCNJ2 | Kir2.1 ($I_{K1}$) | NM 000891 | TTGTCAAGAGCCAAGACACA (SEQ ID NO: 41) AGCAACACACATCTGGGAAT (SEQ ID NO: 42) |
| MLC-2a | | AK311869 | TCAGCTGTATCGACCAGAATCG (SEQ ID NO: 43) AAGACGGTGAAGTTGATGGG (SEQ ID NO: 44) |
| MLC-2v | | NM 000432 | CGTTCGGGAAATGCTGACCACGC (SEQ ID NO: 45) AGTCCAAGTTTCCAGTCACGTCAG (SEQ ID NO: 46) |
| NKX2-5 | | NM 004387 | CCCTGGATTTTGCATTCACT (SEQ ID NO: 47) GGGGACAGCTAAGACACCAG (SEQ ID NO: 48) |
| NPPA | ANF | NM 006172 | ACAGACGTAGGCCAAGAGAG (SEQ ID NO: 49) GTCTGACCTAGGAGCTGGAA (SEQ ID NO: 50) |
| SCN5A | Nav1.5 ($I_{Na}$) | NM 000335 | AGCTCTGTCACGATTTGAGG (SEQ ID NO: 51) AGGACTCACACTGGCTCTTG (SEQ ID NO: 52) |
| TBX2 | | NM 005994 | CTGGACAAGAAGGCCAAGTA (SEQ ID NO: 53) GCATGGAGTTTAGGATGGTG (SEQ ID NO: 54) |
| TBX3 | | NM 016569 | ATTTCACAATTCTCGGTGGA (SEQ ID NO: 55) TATAATTCCCCTGCCACGTA (SEQ ID NO: 56) |
| TBX5 | | NM 080718 | TCCAGAAACTCAAGCTCACC (SEQ ID NO: 57) TGGCAAAGGGATTATTCTCA (SEQ ID NO: 58) |

Example 3

Western Blot Analysis of Akt and Erk Phosphorylation

To demonstrate functional NRG1/ErbB signaling in hESC-CM cultures, two effectors in this signal transduction cascade, the Akt and Erk kinases, were analyzed by western blotting. For this, hESC-CMs (~5×10$^6$ million per well) were treated on day 10 post-induction with 0, 10, or 100 ng/ml NRG-1β (R&D Systems) in the presence or absence of 25 μg/ml anti-NRG1β neutralizing antibody (R&D Systems) for 10 minutes. After treatment, cells were rinsed twice with ice-cold PBS and lysed for 20 minutes on ice with 250 μl of extraction buffer (25 mM Tris-HCl (pH 7.4), 150 mM NaCl, 2 mM EDTA, 10 mM Na$_2$SO$_4$, and 1% Triton X-100 supplemented just prior to use with 50 mM NaF, 1 mM sodium orthovanadate, 1 mM phenylmethylsulfonyl fluoride, and a protease inhibitor cocktail (Sigma)). Lysates were collected with a cell scraper, placed in microcentrifuge tubes, vortexed for 3 minutes at 4° C., and then spun at 4° C. for 20 minutes at 12,000 g to discard cell debris. The resultant protein lysates were then denatured at 95° C. for 10 minutes and loaded (at 30 μg/lane) onto a denaturing 10% SDS/polyacrylamide gel, electrophoresed, and then transferred onto a PVDF membrane. The PVDF blot was blocked for 1 hour at room temperature in 1×TBST (150 mM NaCl, 10 mM Tris-HCl (pH 7.4), and 0.1% Tween) plus 5% nonfat milk, probed overnight with anti-phosphorylation Akt and anti-phosphorylation Erk1/2 antibodies (Cell Signaling), and then incubated with peroxidase-conjugated goat anti-mouse IgG antibody (Sigma). The resultant bands were visualized using an enhanced chemiluminescent detection kit (Amersham). The membrane was then stripped and exposed to total Akt and Erk antibodies (Cell Signaling) to detect total Akt and Erk.

Example 4

Current-Clamp Studies

At 14 days following induction with activin A, hESC-CMs were dispersed using 0.1 U/ml of dispase (Invitrogen) with 63 U/ml DNase I (Invitrogen) and replated at low density onto 0.5% gelatin-coated glass coverslips. After a few days of additional culture, the spontaneously generated action potentials (APs) of the hESC-CMs were recorded using a HEKA EPC-10 amplifier (HEKA, Lambrecht, Germany), operated in current-clamp mode. Note that the EPC-10 has a true "voltage follower" circuit, similar to a classical microelectrode amplifier (Magistretti et al., "Modalities of Distortion of Physiological Voltage Signals by Patch-Clamp Amplifiers: a Modeling Study," *Biophys J.* 74(2 Pt 1):831-842 (1998) and Magistretti et al., "Action Potentials Recorded with Patch-Clamp Amplifiers: Are They Genuine?" *Trends Neurosci.* 19(12):530-534 (1996), which are hereby incorporated by reference in their entirety). After obtaining gigaohm seal, electrical access to the cells was obtained via the β-escin perforated patch technique (Fan et al., "Perforated Patch Recording with Beta-escin," *Pflugers Arch.* 436(6):1021-1023 (1998) and Fu et al., "Perforated Patch Recording of L-type Calcium Current with Beta-escin in Guinea Pig Ventricular Myocytes," *Acta Pharmacol Sin.* 24(11):1094-1098 (2003), which are hereby incorporated by reference in their entirety), which was found to improve the success relative to the conventional ruptured patch approach, as it greatly minimized both seal disruption and rundown. Patch pipettes with a resistance of 2-4 MΩ were used; cells with a series resistance of >10 MΩ were discarded. The capacitance of the examined cells was 17.5±7.6 pF (range 5.8-32.8 pF), in comparison to the ~150 pF typically reported for adult human ventricular myocytes (Drouin et al., "Electrophysiologic Characteristics of Cells Spanning the Left Ventricular Wall of Human Heart: Evidence for Presence of M Cells," *J Am Coll Cardiol.* 26(1):185-192 (1995), which is hereby incorporated by reference in its entirety). All recordings were performed at 36±1° C., using the following bath medium: (in mM) 140 NaCl, 5.4 KCl, 1.8 CaCl$_2$, 1.0 MgCl$_2$, 0.33 NaH$_2$PO$_4$, 5 dextrose, and 10 HEPES, adjusted to pH 7.40 with NaOH. The pipette solution was (in mM) 135 KCl, 5 Na$_2$ creatine phosphate, 5 MgATP and 10 HEPES, adjusted to pH 7.20 with KOH. Data were digitized at 10 Hz and filtered at 2.9 Hz. Action potential parameters were analyzed by an individual blinded to culture conditions, using Patchmaster (HEKA) and Igor Pro software.

Example 5

Generation and Use of the cGATA6-EGFP Lentiviral Vector

The pPD46.21 plasmid containing the proximal (−1.5/+0.0) promoter-enhancer region of the chicken GATA6 (cGATA6) gene was generously provided by Dr. John Burch (Fox Chase Cancer Center) (Davis et al. "A GATA-6 Gene Heart-Region-Specific Enhancer Provides a Novel Means to Mark and Probe a Discrete Component of the Mouse Cardiac Conduction System," *Mech Dev.* 108(1-2):105-119 (2001), which is hereby incorporated by reference in its entirety). To generate the cGATA6-EGFP lentiviral vector, the 1.5 kb cGATA6 promoter-enhancer region was excised from the pPD46.21 plasmid by digestion with the restriction enzymes Sal I and Age I. This promoter-enhancer fragment was ligated into the lentiviral transfer plasmid pJGL2-EGFP (generously provided by Drs. Jonathan Golob and Charles Murry, University of Washington), which includes a transgene in which EGFP expression is driven by the constitutive elongation factor-1α (EF1α) promoter, a central polypurine tract, and a woodchuck hepatitis virus post-transcriptional regulatory element (Barry et al., "Lentivirus Vectors Encoding Both Central Polypurine Tract and Posttranscriptional Regulatory Element Provide Enhanced Transduction and Transgene Expression," *Hum Gene Ther.* 12(9):1103-1108 (2001), which is hereby incorporated by reference in its entirety). For this, the EF1α promoter DNA was excised from pJGL2-eGFP plasmid, also using Sal I and Age I digestion, followed by replacement by the cGATA6 promoter-enhancer fragment.

VSV-G-pseudotyped lentiviral particles were generated and concentrated as previously described (Barry et al., "Lentivirus Vectors Encoding Both Central Polypurine Tract and Posttranscriptional Regulatory Element Provide Enhanced Transduction and Transgene Expression," *Hum Gene Ther.* 12(9):1103-1108 (2001) and Li et al., "Stable Transduction of Myogenic Cells with Lentiviral Vectors Expressing a Minidystrophin," *Gene Ther.* 12(14):1099-1108 (2005), which are hereby incorporated by reference in their entirety). In brief, 6×10$^6$ HEK293D cells seeded on a 15 cm$^2$ plate 24 hours prior to co-transfection with the following plasmids: 8 μg of envelope plasmid pMK-VSVG, 15 μg of pMDL-G/P-RPE plasmid expressing the HIV-1 gap/pol and tat genes, 11.5 μg of pRSV-REV plasmid expressing the HIV-1 rev protein, and 29 μg of either the cGATA6-EGFP or EF1α-EGFP lentiviral transfer vector construct. Supernatant containing the resultant viral particles was collected at 72 hours following transfection, concentrated by filtration (Millipore Centricon Plus-20 columns with a molecular weight cutoff of 10 kD), and stored at −80° C. Lentiviral stocks were titered by viral p24$^{gag}$ ELISA (QuickTiter Lentiviral Quantitation kit, Cell Biolabs).

Prior to lentiviral transduction, hESC-CMs were replated onto glass coverslips as described for electrophysiological studies and allowed to recover for 4-5 days. Cells were then exposed to cGATA6-EGFP lentivirus (at 5000 LPs/cell, added to their usual RPMI-B27 medium) for 12 hours. Parallel transduction with an equivalent quantity of the constitutively-expressing EF1α-EGFP lentiviral vector was routinely performed and indicated that this viral titer results in the reliable transduction of ~50% of target hESC-CMs. Transduced cell preparations were then used in either electrophysiological or immunocytochemical studies at 3-4 days post-transduction.

Example 6

Immunocytochemistry

Dissociated hESC-CMs were cultured on glass cover slips, fixed, and immunostained as previously described (Laflamme et al., "Cardiomyocytes Derived from Human Embryonic Stem Cells in Pro-Survival Factors Enhance Function of Infarcted Rat Hearts," *Nat. Biotechnol.* 25(9):1015-1024 (2007), McDevitt et al., "Proliferation of Cardiomyocytes Derived from Human Embryonic Stem Cells is Mediated Via the IGF/PI 3-Kinase/Akt Signaling Pathway," *J Mol Cell Cardiol.* 39(6):865-873 (2005), Laflamme et al., "Formation of Human Myocardium in the Rat Heart from Human Embryonic Stem Cells," *Am J. Pathol.* 167(3):663-671 (2005), and Minami et al., "Extracardiac Progenitor Cells Repopulate Most Major Cell Types in the Transplanted Human Heart," *Circulation* 112(19):2951-2958 (2005), which are hereby incorporated by reference in their entirety). Immunocytochemistry was performed with primary antibodies directed against α-sarcomeric actin (clone 5C5, Sigma, 1:2500 titer), troponin T cardiac isoform Ab-1 (clone 13-11, Thermo Scientific, 1:100), HCN4 (clone N114/10, UC Davis/NIH NeuroMab facility, 1:100), and EGFP (Novus Biologicals, 1:1000), and the β-myosin heavy chain isoform (clone A4.951, American Type Culture Collection, 1:10). Unless otherwise stated, EGFP expression was confirmed in all studies using the aforementioned anti-EGFP antibody. Detection was performed using Alexa-488 or -594 conjugated secondary antibodies (Molecular Probes). All cell counts were performed by an observer blinded as to preceding treatment conditions. Each experimental condition was assayed in triplicate, and a minimum of 500 nuclei were counted per sample.

Example 7

Statistics

When analyzing the proportion of hESC-CMs exhibiting each action potential phenotype under various treatment conditions, groups were compared using Fisher's exact test with Bonferroni correction (with α=0.05 for significance). In the statistical analysis of all other experiments, ANOVA followed by post hoc Student's t-testing with Bonferroni correction was used. Values are expressed as means±standard error, unless otherwise stated.

Figure 1B:
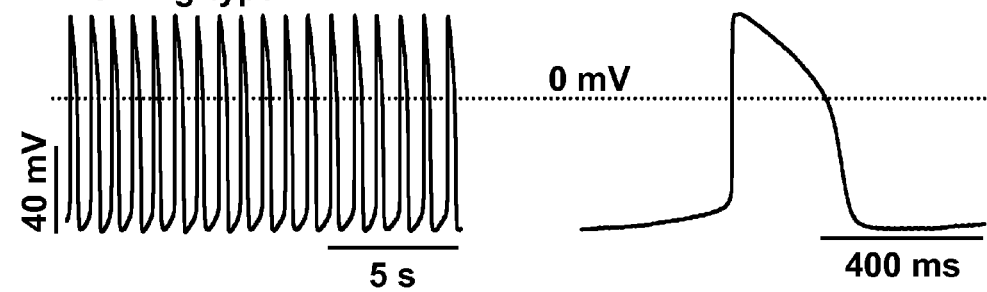

Example 8 hESC-CMs Include Cardiomyocytes with Distinct Nodal and Working (Chamber)-Type Action Potential Phenotypes The spontaneous action potential (AP) properties of hESC-CMs resulting from the standard directed cardiac differentiation protocol (Laflamme et al., "Cardiomyocytes Derived from Human Embryonic Stem Cells in Pro-Survival Factors Enhance Function of Infarcted Rat Hearts," *Nat. Biotechnol.* 25(9):1015-1024 (2007), which is hereby incorporated by reference in its entirety) were characterized. Previous studies have reported that hESC-CMs exhibit distinct either nodal or working-type AP phenotypes (He et al., "Human Embryonic Stem Cells Develop into Multiple Types of Cardiac Myocytes: Action Potential Characterization," *Circ Res.* 93(1):32-39 (2003), Mummery et al., "Differentiation of Human Embryonic Stem Cells to Cardiomyocytes: Role of Co-culture with Visceral Endoderm-Like Cells," *Circulation* 107 (21):2733-2740 (2003), and Moore et al., "Distinct Cardiogenic Preferences of Two Human Embryonic Stem Cell (hESC) Lines are Imprinted in Their Proteomes in the Pluripotent State," *Biochem Biophys Res Commun.* 372(4):553-558 (2008), which are hereby incorporated by reference in their entirety), but these studies have typically examined cardiomyocytes generated by microdissecting spontaneously beating foci from embryoid body-derived preparations of relatively low cardiac purity. While the latter approach could potentially favor cells with greater automaticity, the greater cardiac purity of the preparations described herein allowed the analysis of all cells in an unbiased fashion, rather than focusing on cells with greater spontaneity or a particular morphology. In this initial survey, current-clamp techniques were used to record spontaneous APs from a total of 49 cells, of which only four showed AP characteristics deemed inconsistent with cardiomyocytes (i.e., an AP duration to 90% repolarization (APD$_{90}$) of <20 ms). The remaining 45 cells all showed typical cardiac-type APs with distinct nodal- or working-type characteristics (FIGS. 1A and 1B).

To establish objective criteria for this classification, histogram plots for a variety of parameters including spontaneous firing rate, APD, upstroke velocity (dV/dt$_{max}$), AP amplitude (APA), and maximal diastolic potential (MDP) were analyzed. In this analysis, there was a clear-cut bimodal distribution with regard to dV/dt$_{max}$, with a cutoff between the two populations of ~15 V/s. Table 1 summarizes the AP parameters for the two populations defined using this threshold (i.e., defining cells with a dV/dt$_{max}$<15 V/s as nodal, and those with dV/dt$_{max}$>15 V/s as working-type). Using this criterion, 31% (14 of 45 cells) were classified as nodal-type, with these cells showing a substantially greater spontaneous firing frequency, a smaller APA, and a more depolarized MDP than did the majority population of working-type cardiomyocytes. Although other investigators have further stratified ESC-CMs into atrial, ventricular, and even Purkinje fiber cardiomyocytes, the electrophysiological distinctions between some of these subtypes are known to be subtle at this state of maturation and were not obvious when analyzing the AP data. Therefore, it was decided to focus on the unambiguous electrophysiological differences between nodal and working-type hESC-CMs.

Example 9

Activation of the cGATA6-EGFP Transgene Identifies hESC-CMs with the Nodal Phenotype While AP phenotyping under current-clamp is considered the "gold-standard" method of determining cardiac subtype, a higher throughput, molecular approach to phenotyping was developed. Since no validated markers for early human nodal cells were available, the hypothesis that the activation of a proximal promoter-enhancer element from the chicken GATA6 (cGATA6) gene would specifically identify nodal-type hESC-CMs was tested. In a series of elegant fate-mapping studies in transgenic mice, it has been demonstrated that this promoter element is selectively activated in the atrioventricular (AV) node and the bundle of His of the adult heart (Davis et al., "A GATA-6 Gene Heart-Region-Specific Enhancer Provides a Novel Means to Mark and Probe a Discrete Component of the Mouse Cardiac Conduction System," Mech Dev. 108(1-2):105-119 (2001), which is hereby incorporated by reference in its entirety). Moreover, the cGATA6 promoter is active very early in cardiac development, showing preferential activity in regions of the cardiac crescent and heart tube fated to contribute to nodal structures (Davis et al., "A GATA-6 Gene Heart-Region-Specific Enhancer Provides a Novel Means to Mark and Probe a Discrete Component of the Mouse Cardiac Conduction System," Mech Dev. 108(1-2):105-119 (2001), which is hereby incorporated by reference in its entirety), as well as in nodal cells derived from murine ESCs (White et al., "Embryonic Stem Cells Form an Organized, Functional Cardiac Conduction System In Vitro," Am J Physiol Heart Circ Physiol. (2004), which is hereby incorporated by reference in its entirety).

Figures 2A, 2B, 2C, 2D:
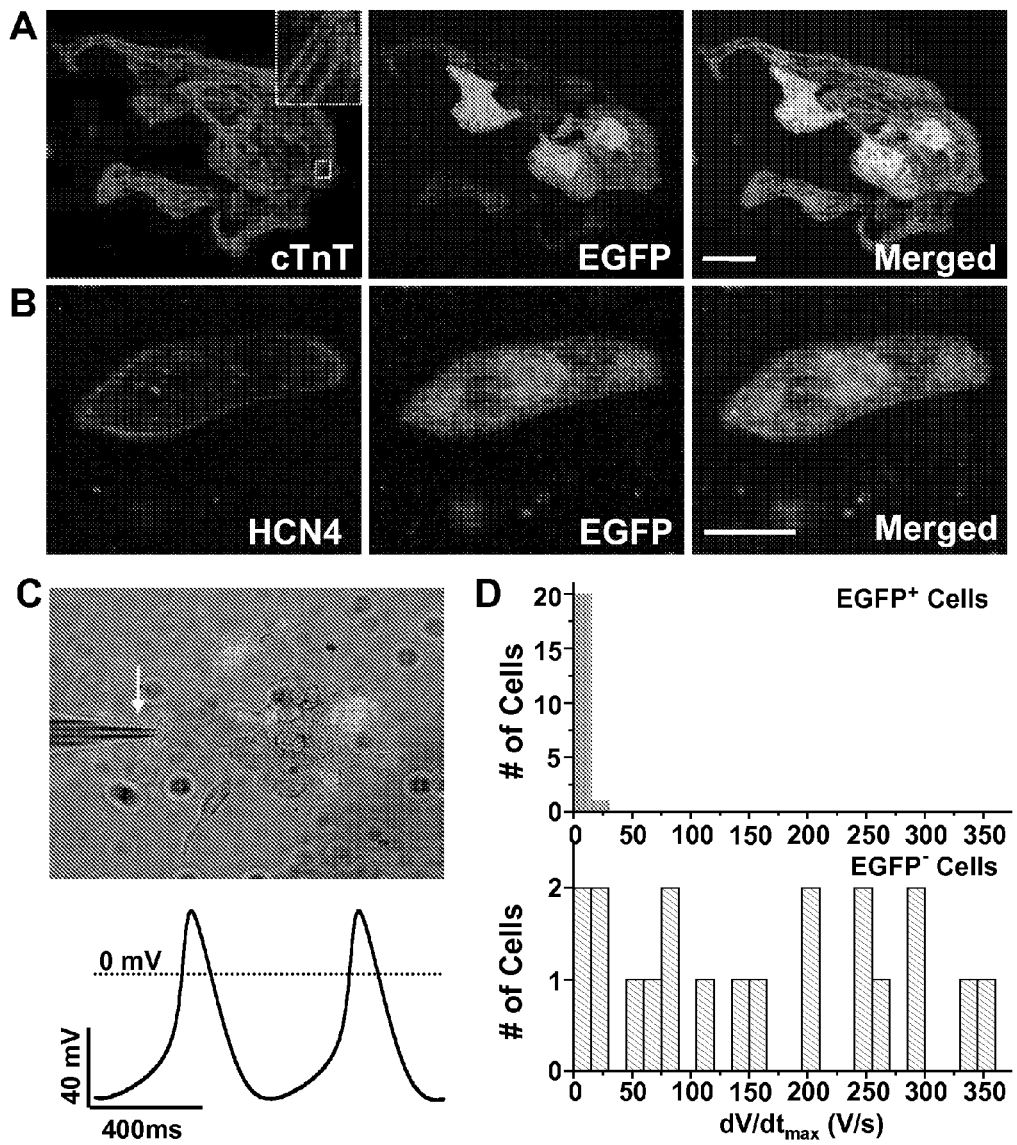
FIGS. 2A-2D show that activation of the cGATA6-EGFP transgene identifies hESC-derived cardiomyocytes with a nodal phenotype. hESC-CM cultures were transduced with a lentiviral vector in which the nodal-specific cGATA6 promoter drives expression of EGFP. About 50% of the cells were transduced, and, by 72 hours post-transduction, ~15% of the total cell population showed EGFP expression. cGATA6-EGFP+ cells expressed the cardiac marker troponin T (cTnT) (FIG. 2A, left panel) and the pacemaker ion channel HCN4 (FIG. 2B, left panel). EGFP expression was confirmed using an anti-EGFP antibody (FIGS. 2A and 2B, middle panels). An overlay of cTnT or HCN4 expression with EGFP is shown in the right panels of FIGS. 2A and 2B, respectively. Scalebar=20 µm.
Figures 6A, 6B:
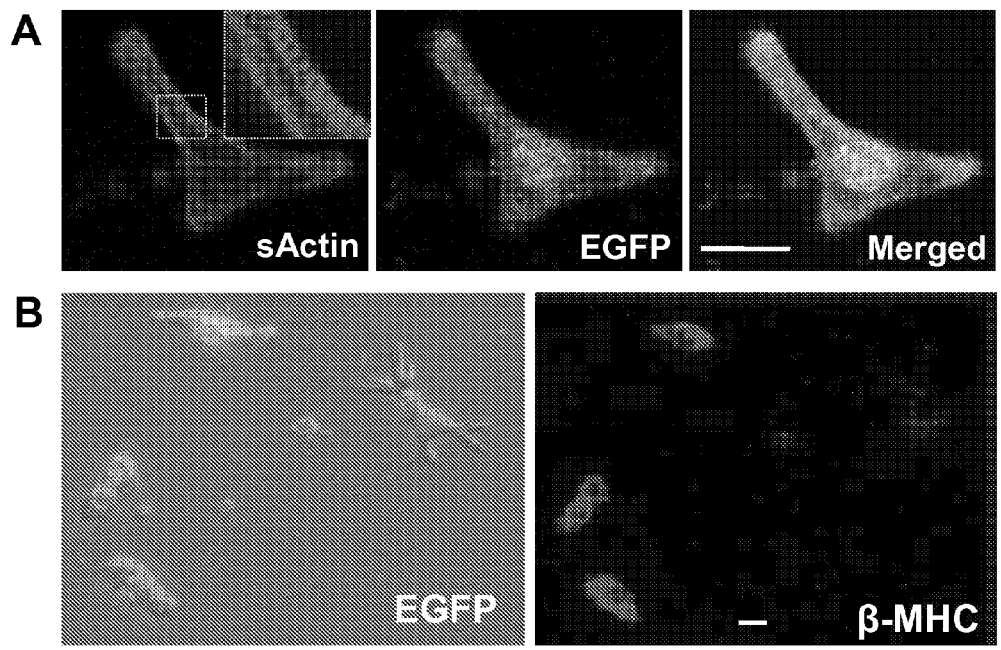
FIGS. 6A-6B demonstrate that cGATA6-EGFP positive cells always express cardiac markers. The left panel of FIG. 6A shows representative immunofluorescence images of EGFP+ cells expressing the striated muscle-marker sarcomeric actin (sActin). EGFP expression is shown in the middle panel of FIG. 6A and a merged image showing co-localization of sActin and EGFP expression in depicted in the right panel of FIG. 6A.

To test its function in hESC-CMs, the latter cultures were transduced with a lentiviral vector in which the proximal cGATA6 promoter drives expression of EGFP. Approximately 15% of the resultant cells were EGFP+, and all of the EGFP+ cells immunostained positively for cardiac markers such as cardiac troponin T (FIG. 2A), sarcomeric actins, and β-myosin heavy chain (β-MHC) (FIGS. 6A and 6B). The EGFP$^+$ cells also uniformly expressed the hyperpolarization-activated, pacemaking ion channel gene HCN4 (FIG. 2B), which is perhaps the best validated and earliest expressed nodal cell marker (Garcia-Frigola et al., "Expression of the Hyperpolarization-Activated Cyclic Nucleotide-Gated Cation Channel HCN4 During Mouse Heart Development," Gene Expr Patterns. 3(6):777-783 (2003) and Shi et al., "Distribution and Prevalence of Hyperpolarization-Activated Cation Channel (HCN) mRNA Expression in Cardiac Tissues," Circ Res. 85(1):e1-6 (1999), which are hereby incorporated by reference in their entirety). Next, the electrophysiological phenotype of the EGFP$^+$ and EGFP$^-$ cells was compared. Consistent with the hypothesis that activation of the cGATA6-EGFP transgene would preferentially identify nodal cells, 95% (20 of 21) of EGFP+ cells showed a nodal-type AP phenotype, versus only 10% (2 of 20) of the EGFP− cells (FIGS. 2C and 2D). Note that only ~50% of hESC-CMs were transduced by the lentiviral vector in these experiments. It is therefore possible that some or all of the small number of EGFP− myocytes with the nodal phenotype actually represent non-transfected cells. Furthermore, if one corrects for this transduction efficiency, the proportion of cGATA6-EGFP+ putative nodal cells under each condition is in good agreement with that estimated by AP phenotyping.

Example 10 hESC-CMs Exhibit Intact NRG-1β/ErbB Signaling

Figures 3A, 3B, 3C, 3D:
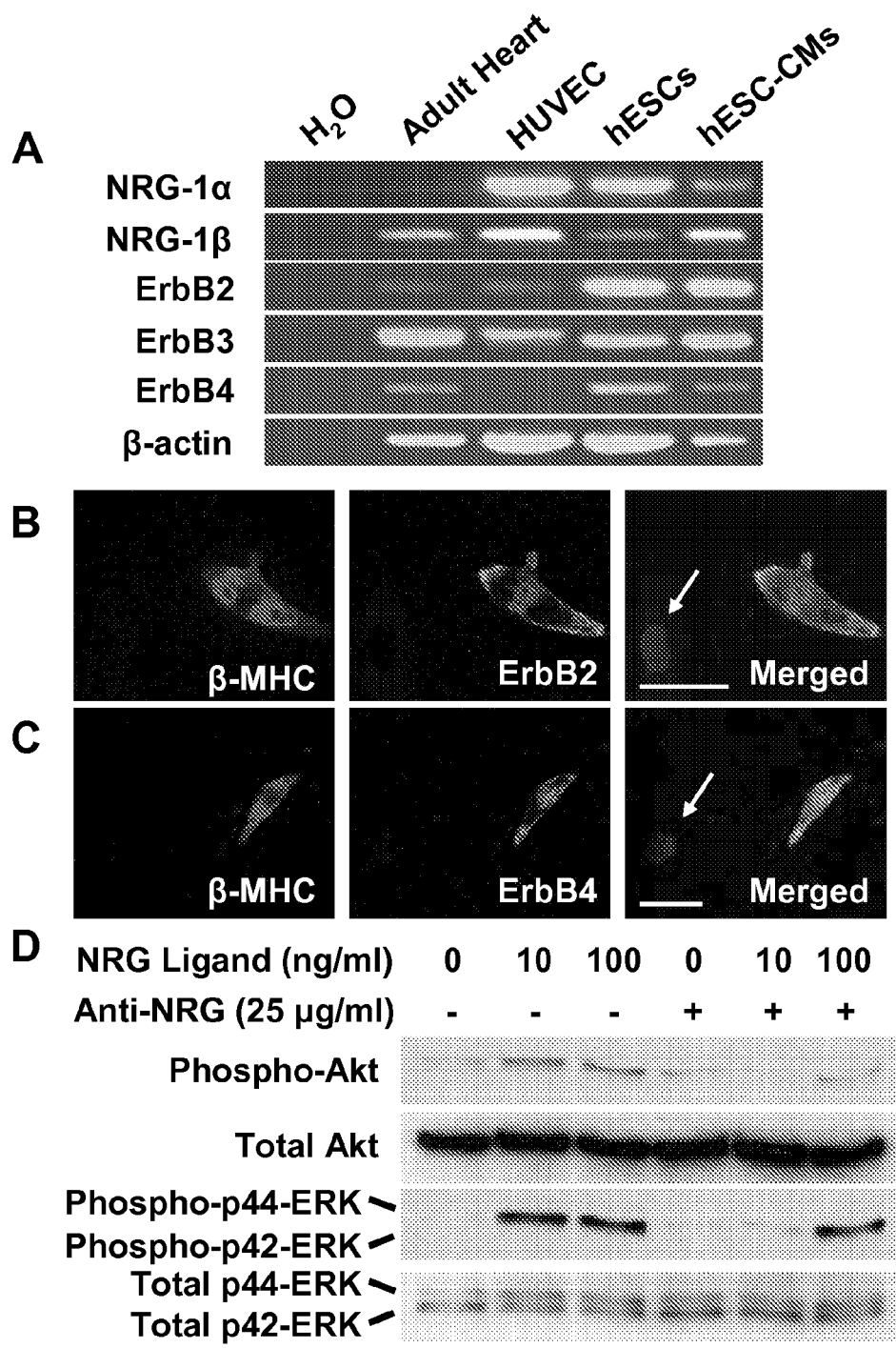
FIGS. 3A-3D demonstrate that hESC-derived cardiomyocytes exhibit an intact NRG-1/ErbB signaling pathway. RT-PCR analysis confirming expression of the α and β isoforms of NRG-1, as well as ErbB2, ErbB3, and ErbB4 receptors in both undifferentiated hESC and hESC-CM cultures is shown in FIG. 3A. Adult human heart and human umbilical vein endothelial cells (HUVECs) were examined as positive controls.

Next, studies to demonstrate a functional NRG-1β/ErbB signaling system in hESC-CM cultures were conducted. RT-PCR analysis confirmed the expression of NRG-1 agonist as well as ErbB2, ErbB3, and ErbB4 receptors in both undifferentiated hESC and differentiated hESC-CM cultures (FIG. 3A). Time-course studies did not reveal any obvious changes in the levels of these transcripts in differentiating cultures from day 0 through day 30 following the induction of cardiogenesis with activin A. To confirm specific expression of the ErbB receptors by the cardiomyocytes themselves, hESC-CM cultures were dual-immunolabeled with antibodies against ErbB2, ErbB4, and the cardiac marker β-MHC. Consistent with prior findings in rodent hearts (Gassmann et al., "Aberrant Neural and Cardiac Development in Mice Lacking the ErbB4 Neuregulin Receptor," Nature 378(6555):390-394 (1995), Lee et al., "Requirement for Neuregulin Receptor erbB2 in Neural and Cardiac Development," Nature 378(6555):394-398 (1995), and Zhao et al., "Neuregulins Promote Survival and Growth of Cardiac Myocytes. Persistence of ErbB2 and ErbB4 Expression in Neonatal and Adult Ventricular Myocytes," J Biol Chem. 273(17):10261-10269 (1998), which are hereby incorporated by reference in their entirety), ErbB2 and ErbB4 were expressed by essentially all of β-MHC$^+$ cardiomyocytes, but only by a small minority (<10%) of the β-MHC− non-cardiac cells (FIGS. 3B and 3C). Finally, functional NRG1/ErbB signaling in hESC-CM cultures was demonstrated by analyzing two proximal effectors in this signal transduction cascade, the Akt and ERK kinases. Both kinases were phosphorylated in response to treatment with NRG1β ligand but this response was inhibited in the presence of an anti-NRG1β neutralizing antibody (FIG. 3D).

Example 11

Figures 4A, 4B, 4C:
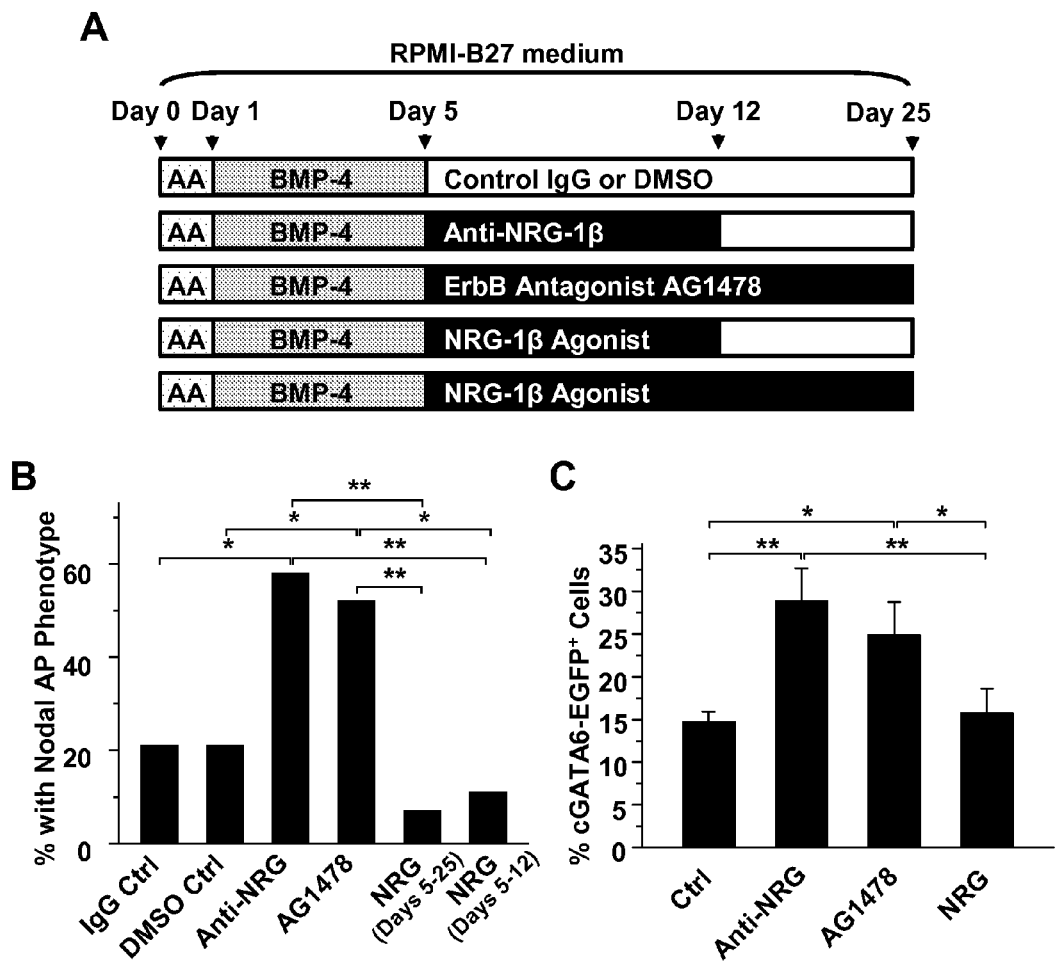
FIGS. 4A-4C demonstrate that interference with NRG-1/ErbB signaling changes the ratio of nodal versus working type cells in differentiating hESC-derived cardiomyocyte cultures.

Inhibition of NRG-1β/ErbB Signaling Enhances the Proportion of hESC-CMs with the Nodal Phenotype To test the hypothesis that the NRG-1β/ErbB signaling system regulates the relative abundance of the two cardiac subtypes in differentiating hESC-CM cultures, cardiac differentiation was induced in the presence of either inhibitors or activators of NRG-1β/ErbB signaling (FIG. 4A.) The AP phenotype of the resultant cells under each condition was then determined by a blinded electrophysiologist, using the criteria described above. As illustrated in FIG. 4B, the inhibition of NRG1/ErbB signaling either with anti-NRG1β neutralizing antibody or the ErbB antagonist AG1478 increased the proportion of cells exhibiting a nodal-like AP phenotype by nearly three-fold: from 21% in control cells to 58% and 52% in anti-NRG113- and AG1478-treated cells, respectively (p<0.05 versus control in both cases). Conversely, there was a trend toward the opposite effect (i.e., a reduction in the fraction of nodal cells) following treatment with exogenous NRG1β ligand, although this did not reach statistical significance after correction for multiple comparisons.

Similar results were obtained using transgenic hESC-CM cultures in which the fraction of nodal-type cells was evaluated by activation of the cGATA6-EGFP transgene (FIG. 4C). Here, the percentage of EGFP+ putative nodal cells increased from 15% in control cultures to 29% in anti-NRG1β- and 25% AG1478-treated cultures (p<0.01 and p<0.05 versus control, respectively). If one again corrects for the ~50% transduction efficiency, the fraction of nodal-type cells estimated by the genetic label under each of these conditions is in reasonable agreement with that obtained by direct AP recordings.

Example 12

Figure 5:
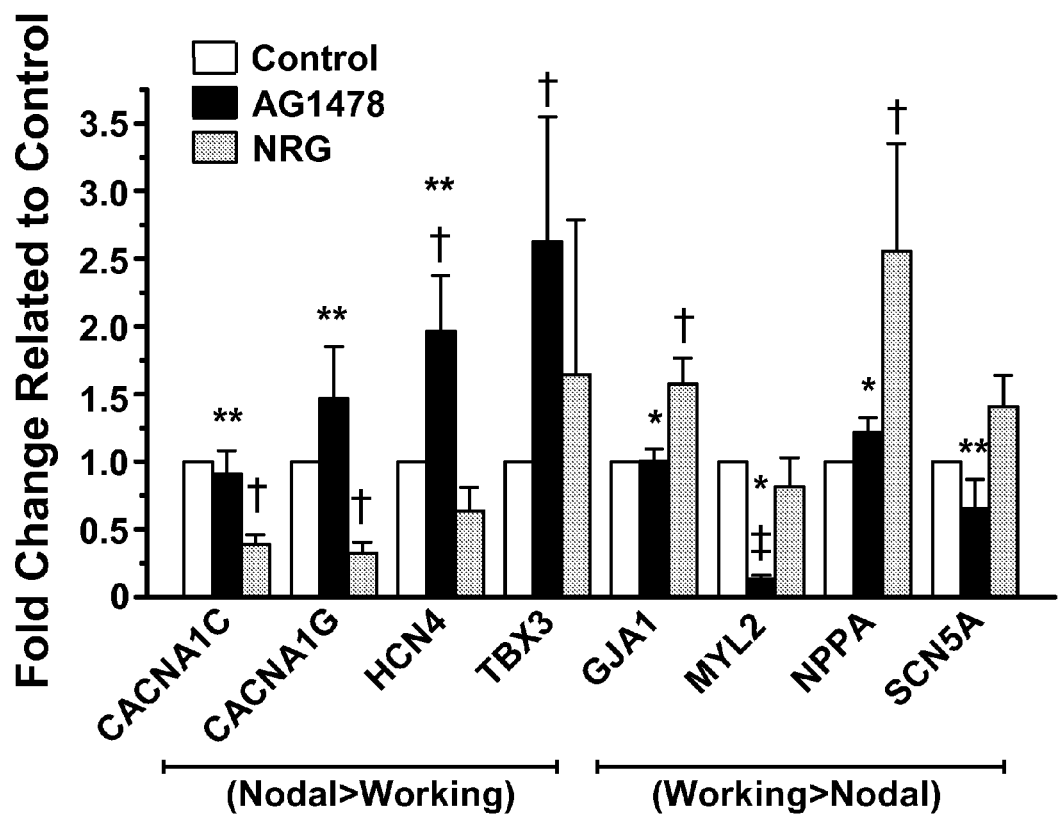
FIG. 5 shows that interference with NRG-1/ErbB signaling changes the expression of cardiac subtype-specific genes. Quantitative RT-PCR analysis of cardiac subtype-specific genes showing differential expression in control, AG1478-, or exogenous NRG-1b-treated hESC-CM cultures. Transcript levels are shown normalized to that in controls. Groups were compared by Bonferroni corrected one-way ANOVA with †P<0.05, ‡P<0.01 vs. control, *P<0.05, **P<0.01 vs. NRG-treated. Labels indicate the anticipated pattern of expression in nodal- and working-type cells. See Table 4 for results from the full panel of genes examined, including those which did not show statistically significant changes.

NRG-1β/ErbB Signaling Regulates the Expression of Cardiac Subtype-Specific Genes In the preceding experiments, manipulation of NRG-1β/ErbB signaling changed the relative abundance of the two cardiac subtypes, as determined by both AP phenotyping and activation of the nodal-specific cGATA6-EGFP genetic reporter. To confirm these findings with an independent, molecular approach, quantitative RT-PCR was used to compare the expression of 18 subtype-specific genes in control, AG1478, and NRG-1β ligand-treated hESC-CM cultures (see Table 4). Note that radical changes in gene expression between these conditions were not expected, as all of the treatment conditions had resulted in a mixture of both cardiac subtypes by AP phenotyping. Nonetheless, the changes in gene expression were remarkably consistent with the previous observations: 8 of the 18 transcripts evaluated were found to be differentially expressed between treatment conditions, and all 8 transcripts shifted in the hypothesized directions (FIG. 5). For example, AG1478-treated hESC-CMs showed 2.6-fold greater expression of the nodal-associated transcription factor Tbx-3 (TBX3) (Horsthuis et al., "Gene Expression Profiling of the Forming Atrioventricular Node Using a Novel tbx3-Based Node-Specific Transgenic Reporter," Circ Res. 105(1):61-69 (2009), which is hereby incorporated by reference in its entirety) than control cells (p<0.01) and 2.0-fold greater expression of HCN4 (p<0.05). Conversely, hESC-CMs treated with exogenous NRG1β showed 2.6-fold greater expression of NPPA (i.e., atrial natriuretic factor, ANF) than controls (p<0.05). ANF is a well-validated marker of early working chamber differentiation (Houweling et al., "Developmental Pattern of ANF Gene Expression Reveals a Strict Localization of Cardiac Chamber Formation in Chicken," Anat Rec. 266(2):93-102 (2002), Houweling et al., "Expression and Regulation of the Atrial Natriuretic Factor Encoding Gene Nppa During Development and Disease," Cardiovasc Res. 67(4):583-593 (2005), and Chuva de Sousa Lopes et al., "Patterning the Heart, A Template for Human Cardiomyocyte Development," Dev Dyn. 235(7):1994-2002 (2006), which are hereby incorporated by reference in their entirety). In sum, activation of NRG-1β/ErbB signaling increased the expression of genes associated with working cardiomyocytes, while its blockade with AG1478 increased the expression of genes associated with the nodal subtype.

TABLE 4

Quantitative RT-PCR Analysis of Cardiac Subtype-Specific Gene Expression in Control, NRG-, and AG1478-hESC-CMs

| Gene | Fold-Change Relative to Control hESC-CMs | | | Hypothesized Expression Patter |
|---|---|---|---|---|
| | NRG-1β hESC-CMs | AG1478 hESC-CMs | Adult Human Heart | |
| CACNA1C | 0.39 ± 0.07* | 0.91 ± 0.17## | 0.62 ± 0.07 | Nodal > Working |
| CACNA1G | 0.25 ± 0.04* | 1.47 ± 0.24## | 0.06 ± 0.06 | Nodal >> Working |
| GJA1 | 1.57 ± 0.02* | 1.00 ± 0.09## | 0.65 ± 0.04 | Working > Nodal |
| GJA5 | 1.13 ± 0.19 | 0.76 ± 0.25 | 1.48 ± 0.11 | Working >> Nodal |
| GJA7 | 1.02 ± 0.41 | 1.06 ± 0.15 | 0.79 ± 0.28 | Nodal > Working |
| HCN1 | 0.72 ± 0.27 | 1.54 ± 0.69 | 0.07 ± 0.04 | Nodal > Working |
| HCN2 | 0.76 ± 0.10 | 1.04 ± 0.32 | 4.63 ± 0.79 | Nodal > Working |
| HCN4 | 0.64 ± 0.17 | 1.96 ± 0.41*## | 0.15 ± 0.05 | Nodal >> Working |
| KCNE1 | 1.04 ± 0.20 | 1.03 ± 0.37 | 1.40 ± 0.37 | Nodal >> Working |
| KCNE2 | 1.56 ± 0.98 | 2.43 ± 2.02 | 0.20 ± 0.06 | Nodal >> Working |
| KCNJ2 | 1.05 ± 0.42 | 0.37 ± 0.18 | 6.96 ± 2.92 | Working >> Nodal |
| MLC-2a | 0.69 ± 0.32 | 1.01 ± 0.42 | 0.24 ± 0.05 | Working > Nodal |
| MLC-2v | 0.81 ± 0.38 | 0.13 ± 0.05**# | 5198 ± 289 | Working > Nodal |
| NKX2.5 | 1.06 ± 0.43 | 1.39 ± 0.78 | 2.17 ± 0.91 | Working > Nodal |
| NPPA | 2.56 ± 0.80* | 1.22 ± 0.11# | 0.26 ± 0.03 | Working >> Nodal |
| SCN5A | 1.41 ± 0.24 | 0.65 ± 0.22## | 6.44 ± 2.35 | Working >> Nodal |
| TBX2 | 0.77 ± 0.17 | 1.58 ± 0.49 | 0.43 ± 0.21 | Nodal > Working |
| TBX3 | 1.64 ± 1.15 | 2.63 ± 0.92 | 1.18 ± 0.29 | Nodal >> Working |
| TBX5 | 0.69 ± 0.14 | 2.41 ± 0.98 | 0.77 ± 0.22 | Working > Nodal |

Fold-gene expression in NRG-1β-treated hESC-CMs, AG1478-treated hESC-CMs, and adult human in all cases normalized to expression to control (untreated) hESC-CMs. The primers used in this study listed above in Table 3.
Values are mean ± SE (from 4 biological replicates).
Expression in hESC-CM groups were compared by Bonferroni corrected one-way ANOVA with
*P < 0.05 vs. control,
**P < 0.01 vs. control,
P < 0.05 vs. NRG-treated, and
P < 0.01 vs. NRG-treated.
Genes that showed at least one statistically significant difference between groups are highlighted and also appear in FIG. 5.
The column to the right indicates the pattern of expression hypothesized before the experiment, based on currently published literature.

Discussion of Examples 1-12

Elegant work in non-human model systems indicates that working- and nodal-type cardiomyocytes can be distinguished at a remarkably early stage during heart development (Christoffels et al., "Architectural Plan for the Heart: Early Patterning and Delineation of the Chambers and the Nodes," Trends Cardiovasc Med. 14(8):301-307 (2004), which is hereby incorporated by reference in its entirety). Working-type myocytes in the nascent atrial and ventricular chambers exhibit greater proliferative activity and more rapid electrical propagation than their nodal counterparts, and they express chamber-specific markers including high-conductance gap junction proteins (connexins-40 and -43) and ANF. Nodal cells show more automaticity and retain a phenotype closer to that of primary myocardium, in part because the transcription factors Tbx2 and Tbx3 repress the chamber-specific gene expression program in these cells (Bakker et al., "Transcription Factor Tbx3 is Required for the Specification of the Atrioventricular Conduction System," Circ Res. 102(11):1340-1349 (2008), Christoffels et al., "T-box Transcription Factor Tbx2 Represses Differentiation and Formation of the Cardiac Chambers," Dev Dyn. 229(4):763-770 (2004), and Hoogaars et al., "The Transcriptional Repressor Tbx3 Delineates the Developing Central Conduction System of the Heart," *Cardiovasc Res.* 62(3):489-499 (2004), which are hereby incorporated by reference in their entirety). That said, a number of positive markers (including activation of the cGATA6 transgene (Davis et al., "A GATA-6 Gene Heart-Region-Specific Enhancer Provides a Novel Means to Mark and Probe a Discrete Component of the Mouse Cardiac Conduction System," *Mech Dev.* 108(1-2):105-119 (2001) and Adamo et al., "GATA-6 Gene Enhancer Contains Nested Regulatory Modules for Primary Myocardium and the Embedded Nascent Atrioventricular Conduction System," *Anat Rec A Discov Mol Cell Evol Biol.* 280(2):1062-1071 (2004), which are hereby incorporated by reference in their entirety) have been reported to distinguish nodal precursors from the remainder of the primary myocardium, and there is increasing evidence for the induction and specialization of nodal cells during development (Horsthuis et al., "Gene Expression Profiling of the Forming Atrioventricular Node Using a Novel tbx3-Based Node-Specific Transgenic Reporter," *Circ Res.* 105(1):61-69 (2009), which is hereby incorporated by reference in its entirety). He et al., "Human Embryonic Stem Cells Develop into Multiple Types of Cardiac Myocytes: Action Potential Characterization," *Circ Res.* 93(1):32-39 (2003), which is hereby incorporated by reference in its entirety, and others have reported that nodal- and working-type cells can also be distinguished in early hESC-CM cultures using electrophysiological techniques (Mummery et al., "Differentiation of Human Embryonic Stem Cells to Cardiomyocytes: Role of Coculture with Visceral Endoderm-Like Cells," *Circulation* 107(21):2733-2740 (2003) and Moore et al., "Distinct Cardiogenic Preferences of Two Human Embryonic Stem Cell (hESC) Lines are Imprinted in Their Proteomes in the Pluripotent State," *Biochem Biophys Res Commun.* 372(4):553-558 (2008), which are hereby incorporated by reference in their entirety). Here, these findings have been confirmed and extended by demonstrating that the AP phenotype of hESC-CMs correlates with the activation of the novel cGATA6 transgene. The above Examples also represent the first electrophysiological analysis of the hESC-CMs that result from the recently reported directed differentiation system (Laflamme et al., "Cardiomyocytes Derived from Human Embryonic Stem Cells in Pro-Survival Factors Enhance Function of Infarcted Rat Hearts," *Nat. Biotechnol.* 25(9):1015-1024 (2007), which is hereby incorporated by reference in its entirety).

This cell culture system was also used to investigate the regulation by NRG-1β/ErbB signaling of cardiac subtype specification in differentiating human cardiomyocytes. Using three independent approaches (AP phenotyping, activation of the cGATA6-EGFP reporter, and RT-PCR analysis of subtype-specific genes), it was demonstrated that the inhibition of this signaling pathway results in a ~2-3 fold increase in the proportion of hESC-CMs exhibiting the nodal phenotype. Note there was a trend toward the opposite effect based on AP phenotyping (i.e., a decrease in the fraction of nodal cells following treatment exogenous NRG-1β). Given the findings of abundant endogenous NRG-1β transcript in hESC-CM cultures throughout the differentiation process, it can be inferred that ErbB activation promotes the differentiation ("ventricularization") and/or expansion of working-type cardiomyocytes, but that this process may be largely saturated by endogenous agonist under control conditions. Conversely, when endogenous NRG-1β/ErbB signaling is antagonized, a majority of the resultant hESC-CMs show the nodal phenotype.

In the developing mouse heart, NRG-1β/ErbB signaling has been implicated in two anatomically and temporally distinct steps: 1) the maturation and expansion of the primitive ventricle (Meyer et al., "Multiple Essential Functions of Neuregulin in Development," *Nature* 378(6555):386-390 (1995), Kramer et al., "Neuregulins with an Ig-Like Domain are Essential for Mouse Myocardial and Neuronal Development," *Proc Natl Acad Sci USA* 93(10):4833-4838 (1996), Zhao et al., "Selective Disruption of Neuregulin-1 Function in Vertebrate Embryos Using Ribozyme-tRNA Transgenes," *Development* 125(10):1899-1907 (1998), Gassmann et al., "Aberrant Neural and Cardiac Development in Mice Lacking the ErbB4 Neuregulin Receptor," *Nature* 378(6555):390-394 (1995), Lee et al., "Requirement for Neuregulin Receptor erbB2 in Neural and Cardiac Development," *Nature* 378(6555):394-398 (1995), Corfas et al., "Differential Expression of ARIA Isoforms in the Rat Brain," *Neuron* 14(1):103-115 (1995), and Hertig et al., "Synergistic Roles of Neuregulin-1 and Insulin-Like Growth Factor-I in Activation of the Phosphatidylinositol 3-Kinase Pathway and Cardiac Chamber Morphogenesis," *J Biol Chem.* 274(52):37362-37369 (1999), which are hereby incorporated by reference in their entirety), and 2) the subsequent induction of working-type (specifically ventricular) cardiomyocytes into the peripheral conduction system (Rentschler et al., "Neuregulin-1 Promotes Formation of the Murine Cardiac Conduction System," *Proc Natl Acad Sci USA* 99(16):10464-10469 (2002) and Patel et al., "Endothelin-1 and Neuregulin-1 Convert Embryonic Cardiomyocytes into Cells of the Conduction System in the Mouse," *Dev Dyn.* 233(1):20-28 (2005), which are hereby incorporated by reference in their entirety). The findings described herein are entirely consistent with the former process, that is, the activation of NRG-1β/ErbB signaling promotes the recruitment of early working-type hESC-CMs. Additional mechanistic studies are required, but this preliminary data suggests NRG-1β/ErbB signaling regulates differentiation into the working subtype, rather than merely differentially affecting the proliferation or survival of one subtype or another. It would be interesting to examine whether NRG-1β treatment of later working-type hESC-CMs induces specific Purkinje fiber differentiation, but there is a lack validated markers for human Purkinje fibers at this developmental stage.

At first glance, the findings described herein may seem to contradict two prior studies in non-human models that suggest NRG-1β treatment actually induces nodal differentiation. First, based on calcium imaging studies of zebrafish embryos in which NRG was knocked-down by morpholino antisense oligonucleotides, Milan et al. concluded that NRG was involved in the patterning of the slow-conducting nodal tissue of the AV ring (Milan et al., "Notch1b and Neuregulin are Required for Specification of Central Cardiac Conduction Tissue," *Development* 133(6):1125-1132 (2006), which is hereby incorporated by reference in its entirety). However, while conduction velocity in the AV node appeared little changed in the NRG-morphant hearts, propagation in the atrial and ventricular chambers was profoundly slowed (>5-fold). Hence, the most striking phenotypic change following ablation of NRG-1β/ErbB signaling was reduced functional maturation of the rapid-conduction chamber myocardium, an observation consistent with the findings described herein with hESC-CM cultures. Subsequently, Ruhparwar et al. reported that NRG-1β induced a "pacemaker-like" phenotype when applied to murine primary ventricular cardiomyocytes from the late fetal period (Ruhparwar et al., "Enrichment of cardiac pacemaker-like cells: neuregulin-1 and Cyclic AMP Increase I(f)-Current Density and Connexin 40 mRNA Levels in Fetal Cardiomyocytes," *Med Biol Eng Comput.* 45(2):221-227 (2007), which is hereby incorporated by reference in its entirety). This apparent discrepancy can be attributed to imprecision regarding the distinction between nodal (pacemaker) cells and myocytes of the peripheral conduction system (e.g., Purkinje fibers), cell types with unique developmental origins and phenotypic features (Cheng et al., "Development of the Cardiac Conduction System Involves Recruitment Within a Multipotent Cardiomyogenic Lineage," *Development* 126(22):5041-5049 (1999), which is hereby incorporated by reference in its entirety). Cells fated to become Purkinje fibers are recruited from committed working-type cardiomyocytes, not from nodal progenitors. It is possible that Ruhparwar et al induced Purkinje fiber rather than nodal differentiation in their study. In support of this assertion, Ruhparwar emphasized that NRG-1β induced a robust increase in connexin-40 expression. Connexin-40 is a well-accepted early marker of cardiac chamber differentiation (Van Kempen et al., "Developmental Changes of Connexin40 and Connexin43 mRNA Distribution Patterns in the Rat Heart," *Cardiovasc Res.* 32(5):886-900 (1996), Delorme et al., "Developmental Regulation of Connexin 40 Gene Expression in Mouse Heart Correlates with the Differentiation of the Conduction System," *Dev Dyn.* 204(4):358-371 (1995), and Christoffels et al., "Chamber Formation and Morphogenesis in the Developing Mammalian Heart," *Dev. Biol.* 223(2):266-278 (2000), which are hereby incorporated by reference in their entirety), so an increase in its expression would imply induction of working-type myocytes, not "pacemaker-like" cells as interpreted by the authors. However, because connexin-40 expression later becomes restricted to the atria and peripheral conduction system (Miquerol et al., "Gap Junctional Connexins in the Developing Mouse Cardiac Conduction System," *Novartis Found Symp.* 250:80-98; discussion 98-109, 276-109 (2003), which is hereby incorporated by reference in its entirety), it is plausible that NRG-1β treatment induced their cells into the latter phenotype.

Studies are underway to determine the source of the endogenous NRG-1β agonist in the hESC-CM cultures described herein. In the developing mouse heart, NRG-1β is known to be released by the endocardium (Meyer et al., "Multiple Essential Functions of Neuregulin in Development," *Nature* 378(6555):386-390 (1995), Kramer et al., "Neuregulins with an Ig-Like Domain are Essential for Mouse Myocardial and Neuronal Development," *Proc Natl Acad Sci USA* 93(10): 4833-4838 (1996), Zhao et al., "Selective Disruption of Neuregulin-1 Function in Vertebrate Embryos Using Ribozyme-tRNA Transgenes," *Development* 125(10):1899-1907 (1998), and Corfas et al., "Differential Expression of ARIA Isoforms in the Rat Brain," *Neuron* 14(1):103-115 (1995), which are hereby incorporated by reference in their entirety), but there were vanishingly few endothelial cells in the hESC-CM cultures used in the studies described above. Interestingly, Mercola and colleagues have recently reported that highly purified hESC-CMs, produced by genetic selection, show less ventricular maturation than do hESC-CMs in embryoid body preparations of low cardiac purity (Kita-Matsuo et al., "Lentiviral Vectors and Protocols for Creation of Stable hESC Lines for Fluorescent Tracking and Drug Resistance Selection of Cardiomyocytes," *PLoS One* 4(4):e5046 (2009), which is hereby incorporated by reference in its entirety). The findings described herein beg the question whether it is the removal of NRG-1β-releasing non-cardiac cells that underlies this effect in their system. If so, it may prove helpful to supplement purified hESC-CMs with exogenous NRG-1β when working-type cardiomyocytes are desired.

To conclude, the studies described herein suggest two complementary approaches for the generation of subtype-enriched hESC-CMs: 1) genetic labeling of nodal cells, based on the activation of the proximal cGATA6 promoter, and 2) manipulation of NRG-1β/ErbB signaling, which appears to regulate the relative abundance of nodal and working-type cardiomyocytes. Both approaches are expected to have tremendous utility in cell transplantation studies (e.g., to compare the in vivo behavior of subtype-enriched preparations), as well as in efforts to further elucidate the molecular mechanisms of subtype specification in the developing human heart. It is anticipated that their efficacy in related human cardiac progenitor cell populations, including cardiomyocytes from induced pluripotent stem cells (Zhang et al., "Functional Cardiomyocytes Derived from Human Induced Pluripotent Stem Cells," *Circ Res.* 104(4):e30-41 (2009), which is hereby incorporated by reference in its entirety) and resident cardiac stem cells (Laugwitz et al., "Postnatal isl1+Cardioblasts Enter Fully Differentiated Cardiomyocyte Lineages," *Nature* 433(7026):647-653 (2005) and Messina et al., "Isolation and Expansion of Adult Cardiac Stem Cells from Human and Murine Heart," *Circ Res.* 95(9):911-921 (2004), which are hereby incorporated by reference in their entirety) to be similar.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of producing cardiomyocytes having a nodal/pacemaker phenotype, said method comprising:
    culturing stem cells under conditions effective to produce cardiomyocytes and
    contacting the cardiomyocytes with an antagonist of neuregulin-1 or an antagonist of ErbB under conditions effective to induce production of cardiomyocytes having a nodal/pacemaker phenotype.

2. The method according to claim 1, wherein the stem cells are selected from the group consisting of embryonic stem cells, adult stem cells, and induced pluripotent stem cells.

3. The method according to claim 1, wherein the stem cells are human embryonic stem cells.

4. The method according to claim 1, wherein the cardiomyocytes are contacted with an antagonist of neuregulin-1 in the form of an antagonist of neuregulin-1β.

5. The method according claim 1, wherein the cardiomyocytes are contacted with an antagonist of neuregulin-1 in the form of a nucleic acid molecule selected from the group consisting of a neuregulin-1 antisense molecule, siRNA molecule, and shRNA molecule.

6. The method according to claim 1, wherein the cardiomyocytes are contacted with an antagonist of neuregulin-1 in the form of an anti-neuregulin-1β antibody or a binding fragment thereof, or a neuregulin-1 aptamer.

7. The method according to claim 1, wherein the cardiomyocytes are contacted with an antagonist of ErbB in the form of a nucleic acid molecule selected from the group consisting of an ErbB antisense molecule, siRNA molecule, and shRNA molecule.

8. The method according to claim 1, wherein the cardiomyocytes are contacted with an antagonist of ErbB in the form of an anti-ErbB antibody or antibody binding fragment thereof, or an ErbB aptamer.

9. The method according to claim 1, wherein the cardiomyocytes are contacted with an antagonist of ErbB in the form of a recombinant protein or peptide fragment thereof selected from the group consisting of Nrdp1, Kek1, argos, and herstatin.

10. The method according to claim 1, wherein the cardiomyocytes are contacted with an antagonist of ErbB in the form of a small molecule selected from the group consisting of JNJ-28871063, CI-1033, PKI1-66, tryphostin AG825, AG1478, and PD158780.

11. A method of producing cardiomyocytes having an atrial/ventricular phenotype, said method comprising:
    culturing stem cells under conditions effective to produce cardiomyocytes; and contacting the cardiomyocytes with a neuregulin-1 agonist, neuregulin mimetic, or an ErbB receptor agonist under conditions effective to induce the production of cardiomyocytes having an atrial/ventricular phenotype.

12. The method according to claim 11, wherein the stem cells are selected from the group consisting of embryonic stem cells, adult stem cells, and induced pluripotent stem cells.

13. The method according to claim 11, wherein the stem cells are human embryonic stem cells.

14. The method according to claim 11, wherein the cardiomyocytes are contacted with an agonist of neuregulin-1 in the form or an agonist of neuregulin-1β.

15. The method according claim 11, wherein the cardiomyocytes are contacted with an agonist of neuregulin-1 in the form of a recombinant neuregulin-1 protein or peptide fragment thereof.

16. The method according to claim 11, wherein the cardiomyocytes are contacted with an agonist of neuregulin-1 in the form of a nucleic acid molecule encoding a neuregulin-1 protein or a peptide fragment thereof.

17. The method according to claim 11, wherein the cardiomyocytes are contacted with an agonist of ErbB in the form of a recombinant ErbB receptor ligand or ligand fragment.

18. The method according to claim 11, wherein the cardiomyocytes are contacted with an agonist of ErbB in the form of an ErbB receptor agonist antibody.

* * * * *

SEQUENCE LISTING

<160> NUMBER OF SEQ ID NOS: 58

<210> SEQ ID NO 1
<211> LENGTH: 21
<212> TYPE: RNA
<213> ORGANISM: Artificial
<220> FEATURE:
<223> OTHER INFORMATION: Erb2 siRNA

<400> SEQUENCE: 1
cauugugcag aauucguccu u                                             21

<210> SEQ ID NO 2
<211> LENGTH: 21

-continued

```
<212> TYPE: RNA
<213> ORGANISM: Artificial
<220> FEATURE:
<223> OTHER INFORMATION: Erb2 siRNA

<400> SEQUENCE: 2
ccauugugca gaauucgucu u                                              21

<210> SEQ ID NO 3
<211> LENGTH: 21
<212> TYPE: RNA
<213> ORGANISM: Artificial
<220> FEATURE:
<223> OTHER INFORMATION: Erb2 siRNA

<400> SEQUENCE: 3
aaacgugucu guguuguagu u                                              21

<210> SEQ ID NO 4
<211> LENGTH: 21
<212> TYPE: RNA
<213> ORGANISM: Artificial
<220> FEATURE:
<223> OTHER INFORMATION: Erb2 siRNA

<400> SEQUENCE: 4
caucacguau gcuucgucuu u                                              21

<210> SEQ ID NO 5
<211> LENGTH: 21
<212> TYPE: RNA
<213> ORGANISM: Artificial
<220> FEATURE:
<223> OTHER INFORMATION: Erb4 siRNA

<400> SEQUENCE: 5
acugagcucu cucucugacu u                                              21

<210> SEQ ID NO 6
<211> LENGTH: 21
<212> TYPE: RNA
<213> ORGANISM: Artificial
<220> FEATURE:
<223> OTHER INFORMATION: Erb4 siRNA

<400> SEQUENCE: 6
gucagagaga gagcucaguu u                                              21

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
ttgctccagt gaatccaggt t                                              21

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
```
tgaaaagcca ggaatcggct g                                              21

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
cgatcaccag taaactcatt tg                                             22

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tgaaaagcca ggaatcggct g                                              21

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11
ggcataggaa ttttcgtagt acatat                                         26

<210> SEQ ID NO 12
<211> LENGTH: 15
<212> TYPE: DNA
<213> ORGANISM: Artificial
<220> FEATURE:
<223> OTHER INFORMATION: primer

<400> SEQUENCE: 12
gaccctccgg gacgg                                                     15

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
ggggctgggg cagccgctc                                                 19

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggctgctgga cattgacgag                                                20

<210> SEQ ID NO 15
<211> LENGTH: 20
<212> TYPE: DNA
<213> ORGANISM: Artificial

-continued

```
<220> FEATURE:
<223> OTHER INFORMATION: primer

<400> SEQUENCE: 15
caggtctggc aagtatggat                                               20

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
ggagtacaaa ttgccaaggg ta                                            22

<210> SEQ ID NO 17
<211> LENGTH: 25
<212> TYPE: DNA
<213> ORGANISM: Artificial
<220> FEATURE:
<223> OTHER INFORMATION: primer

<400> SEQUENCE: 17
cattgtattc tttttcatct ccttc                                         25

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
ctctgatcat ggcaagtatg gat                                           23

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
caaggccaac cgcgagaaga tgac                                          24

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
aggaaggaag gctggaagag tgc                                           23

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
cagaggctac gatttgagga                                               20
```

```
<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gcttcacaaa gaggtcgtgt                                                 20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
cttcacacca tatgctgtct                                                 20

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
ctgctccacc atgtagctct                                                 20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cttttggagt gaccagcaac                                                 20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
tgaagctgaa catgaccgta                                                 20

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
gcagcctcag ctttacaaat g                                               21

<210> SEQ ID NO 28
<211> LENGTH: 21
<212> TYPE: DNA
<213> ORGANISM: Artificial
<220> FEATURE:
<223> OTHER INFORMATION: primer
```

```
<400> SEQUENCE: 28
gtgacagatg ttggcaggaa t                                              21

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
tctcactcgc atcagaatca                                                20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
aagagcaaag gacacaccac                                                20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gtgacagaaa gcaggggtaa                                                20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
attgccagtg ccagagatac                                                20

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
agctcaagtt cgaggtcttc c                                              21

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
tctccttgtt gcccttagtg a                                              21

<210> SEQ ID NO 35
```

```
<211> LENGTH: 21
<212> TYPE: DNA
<213> ORGANISM: Artificial
<220> FEATURE:
<223> OTHER INFORMATION: primer

<400> SEQUENCE: 35
tgatggtggg aaacctgatt a                                              21

<210> SEQ ID NO 36
<211> LENGTH: 21
<212> TYPE: DNA
<213> ORGANISM: Artificial
<220> FEATURE:
<223> OTHER INFORMATION: primer

<400> SEQUENCE: 36
gttgaggacc aagtcgatga g                                              21

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
caggccagat ttacaggaga                                                20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
gcagaatcag tgtgtgcttg                                                20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
tcatggtgat gattggaatg                                                20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ttatcagggg gacattttga                                                20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
```

```
ttgtcaagag ccaagacaca                                            20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
agcaacacac atctgggaat                                            20

<210> SEQ ID NO 43
<211> LENGTH: 22
<212> TYPE: DNA
<213> ORGANISM: Artificial
<220> FEATURE:
<223> OTHER INFORMATION: primer

<400> SEQUENCE: 43
tcagctgtat cgaccagaat cg                                         22

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
aagacggtga agttgatggg                                            20

<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
cgttcgggaa atgctgacca cgc                                        23

<210> SEQ ID NO 46
<211> LENGTH: 24
<212> TYPE: DNA
<213> ORGANISM: Artificial
<220> FEATURE:
<223> OTHER INFORMATION: primer

<400> SEQUENCE: 46
agtccaagtt tccagtcacg tcag                                       24

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
ccctggattt tgcattcact                                            20

<210> SEQ ID NO 48
<211> LENGTH: 20
<212> TYPE: DNA
```

```
<213> ORGANISM: Artificial
<220> FEATURE:
<223> OTHER INFORMATION: primer

<400> SEQUENCE: 48
ggggacagct aagacaccag                                              20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
acagacgtag gccaagagag                                              20

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
gtctgaccta ggagctggaa                                              20

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
agctctgtca cgatttgagg                                              20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
aggactcaca ctggctcttg                                              20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
ctggacaaga aggccaagta                                              20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
gcatggagtt taggatggtg                                              20
```

```
<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
atttcacaat tctcggtgga                                            20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
tataattccc ctgccacgta                                            20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
tccagaaact caagctcacc                                            20

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
tggcaaaggg attattctca                                            20
```